United States Patent [19]
Kucharczyk et al.

[11] Patent Number: 6,061,587
[45] Date of Patent: *May 9, 2000

[54] METHOD AND APPARATUS FOR USE WITH MR IMAGING

[75] Inventors: John Kucharczyk, Edina, Minn.; Michael E. Moseley, Redwood City, Calif.

[73] Assignee: Regents of the University of Minnesota, Minneapolis, Minn.

[ * ] Notice: This patent is subject to a terminal disclaimer.

[21] Appl. No.: 08/856,894

[22] Filed: May 15, 1997

[51] Int. Cl.$^7$ ........................................................ A61B 5/05
[52] U.S. Cl. ........................ 600/411; 600/411; 600/431; 600/432; 600/433; 604/21; 604/93; 604/151; 604/152; 604/153; 604/154; 604/155
[58] Field of Search .................................... 600/411, 431, 600/432, 433; 604/21, 93, 151, 152, 153, 154, 155

[56] References Cited

U.S. PATENT DOCUMENTS

| | | | |
|---|---|---|---|
| 3,640,269 | 2/1972 | Delgado | 128/2 R |
| 4,448,195 | 5/1984 | LeVeen et al. | 128/344 |
| 4,572,198 | 2/1986 | Codrington | 128/653 |
| 4,694,832 | 9/1987 | Ungerstedt | 128/632 |
| 4,767,973 | 8/1988 | Jacobsen et al. | 318/652 |
| 4,807,620 | 2/1989 | Strul et al. | 128/303.1 |
| 4,824,436 | 4/1989 | Wolinsky | 604/53 |
| 4,827,931 | 5/1989 | Longmore | 128/334 R |
| 4,892,538 | 1/1990 | Aebischer et al. | 604/891.1 |
| 4,922,924 | 5/1990 | Gambale et al. | 128/772 |
| 4,941,874 | 7/1990 | Sandow et al. | 604/60 |
| 4,973,304 | 11/1990 | Graham et al. | 604/48 |
| 4,989,608 | 2/1991 | Ratner | 128/653 A |
| 5,017,566 | 5/1991 | Bodor | 514/58 |
| 5,035,231 | 7/1991 | Kubokawa et al. | 600/411 |
| 5,087,236 | 2/1992 | Morimoto | 493/342 |
| 5,106,455 | 4/1992 | Jacobsen et al. | 156/659.1 |
| 5,106,627 | 4/1992 | Aebischer et al. | 424/424 |
| 5,120,322 | 6/1992 | Davis et al. | 604/265 |
| 5,135,498 | 8/1992 | Kam et al. | 604/140 |
| 5,154,179 | 10/1992 | Ratner | 128/653.4 |
| 5,167,625 | 12/1992 | Jacobsen et al. | 604/891.1 |

(List continued on next page.)

FOREIGN PATENT DOCUMENTS

| | | |
|---|---|---|
| 442329 | 1/1991 | European Pat. Off. ......... G01D 5/18 |
| 0619498 | 10/1994 | European Pat. Off. . |
| 93/15784 | 2/1993 | WIPO ........................... A61M 25/00 |
| 93/15785 | 2/1993 | WIPO ........................... A61M 25/00 |
| 93/15872 | 2/1993 | WIPO ........................... B23P 17/00 |
| 94/27697 | 5/1994 | WIPO ........................... A65M 25/00 |
| 96/33761 | 4/1996 | WIPO ........................... A61M 25/00 |

OTHER PUBLICATIONS

Beucker, A., et al., "First clinical results with a single shot zoom imaging sequence "local Look" for high resolution subsecond interventional MR procedures", Proceedings of the International Society for Magnetic Resonance in Medicine, Fifth Scientifc Meeting and Exhibition, Vancouver, BC, Canada, vol. 2, p. 779, (Apr. 12–18, 1997).

(List continued on next page.)

*Primary Examiner*—Brian L. Casler
*Attorney, Agent, or Firm*—Schwegman, Lundberg, Woessner & Kluth P.A.

[57] ABSTRACT

The invention is an apparatus and method for targeted drug delivery into a living patient using magnetic resonance (MR) imaging. The apparatus and method are useful in delivery to all types of living tissue and uses MR Imaging to track the location of drug delivery and estimating the rate of drug delivery. An MR-visible drug delivery device positioned at an target site (e.g., intracranial delivery) delivers a diagnostic or therapeutic drug solution into the tissue (e.g., the brain). The spatial distribution kinetics of the injected or infused drug agent are monitored quantitatively and non-invasively using water proton directional diffusion MR imaging to establish the efficacy of drug delivery at a targeted location.

22 Claims, 11 Drawing Sheets

U.S. PATENT DOCUMENTS

| | | | |
|---|---|---|---|
| 5,171,217 | 12/1992 | March et al. | 604/53 |
| 5,211,165 | 5/1993 | Dumoulin et al. | 128/653.1 |
| 5,211,166 | 5/1993 | Sepponen | 128/653.5 |
| 5,226,902 | 7/1993 | Bae et al. | 604/892.1 |
| 5,269,882 | 12/1993 | Jacobsen | 156/659.1 |
| 5,270,485 | 12/1993 | Jacobsen | 174/15.1 |
| 5,271,400 | 12/1993 | Dumoulin et al. | 128/653.2 |
| 5,273,622 | 12/1993 | Jacobsen | 156/659.1 |
| 5,318,025 | 6/1994 | Dumoulin et al. | 128/653.2 |
| 5,318,540 | 6/1994 | Athayde et al. | 604/141 |
| 5,375,596 | 12/1994 | Twiss et al. | 128/653.1 |
| 5,419,325 | 5/1995 | Dumoulin et al. | 128/653 |
| 5,451,774 | 9/1995 | Jacobsen | 250/227.24 |
| 5,470,307 | 11/1995 | Lindall | 604/20 |
| 5,487,739 | 1/1996 | Aebischer et al. | 604/890.1 |
| 5,514,092 | 5/1996 | Forman et al. | 604/101 |
| 5,569,197 | 10/1996 | Helmus et al. | 604/96 |
| 5,571,089 | 11/1996 | Crocker | 604/102 |
| 5,573,668 | 11/1996 | Grosh et al. | 210/490 |
| 5,580,575 | 12/1996 | Unger et al. | 424/450 |
| 5,588,961 | 12/1996 | Leone et al. | 604/21 |
| 5,590,654 | 1/1997 | Prince | 128/653.4 |
| 5,607,418 | 3/1997 | Arzbaecher | 604/891.1 |
| 5,704,908 | 1/1998 | Hofmann et al. | 604/21 |
| 5,713,359 | 2/1998 | Dumoulin et al. | 128/653.2 |
| 5,800,392 | 9/1998 | Racchini | 604/96 |
| 5,800,408 | 9/1998 | Strauss et al. | 604/264 |
| 5,868,674 | 2/1999 | Glowinski et al. | 600/410 |

OTHER PUBLICATIONS

Boaz, T.L., et al., "A rabbit model for MR–monitoring of tissue destruction in MR–guided radiofrequency hepatic thermal ablation", Proceedings of the International Society for Magnetic Resonance in Medicine, Fifth Scientific Meeting and Exhibition, Vancouver, BC, Canada, vol. 2, p. 774, (Apr. 12–18, 1997).

Burl, M., et al., "A novel coil for catheters for guide wires", Robert Steiner MRI Unit, Hammersmith Hospital, London, W12 ONN, UK, p. 403.

Coutts, G.A., et al.,"Integrated position tracking and imaging of interventional tools and internal devices using small fiducial receiver coils", Proceedings of the International Society for Magnetic Resonance in Medicine, Fifth Scientific Meeting and Exhibition, Vancouver, BC, Canada, vol. 3, p. 1924, (Apr. 12–18, 1997).

Gohde, S.C., et al., "MR–guided cholecystostomy in a pig: assessment of biplanar, real–time Needle Tracking", Proceedings of the International Society for Magnetic Resonance in Medicine, Fourth Scientific Meeting and Exhibition, New York, USA, vol. 2, p. 892, (Apr. 27–May 3, 19).

Langsaeter, L., et al., "Tracking of an MR–compatible Microendoscope for Interventional MRI of the Paranasal Sinuses", UMDS Radiological Sciences, Guy's Hospital, London, SE1 9RT, UK, p. 1929.

Lu, D., et al., "MR–guided percutaneous ethanol ablation of liver tissue in a 0.2T open MR System: preliminary STudy in Porcine Model", Proceedings of the Internatinal Society for Magnetic Resonance in Medicine, Fourth Scientific Meeting and Exhibition, New York, USA, vol. 2, p. 894, (Apr. 27–May 3, 19).

McKinnon, G., "Tracking and Monitoring the Effects of Interventional MR instruments", Proceedings of the Society of Magnetic Resonance, Third Scientific Meeting and Exhibition, and the European Society for Magnetic Resonance in Medicine and Biology, Twelfth Annual Meeting and Exhibition, Nice, France, p. 490, (Aug. 19–25, 1995).

Melzer, A., et al., "Methodology, Technological Prerequisites and Preliminary Clinical Results of Interventions in a Horizontal Open MRI Unit", Proceedings of the International Society for Magnetic Resonance in Medicine, Fourth Scientific Meeting and Exhibition, New York, USA, vol. 2, p. 897, (Apr. 27–May 3, 19).

Rosen, B.R., et al., "Perfusion Imaging by Nuclear Magnetic Resonance", Magnetic Resonance Quarterly, vol. 5, No. 4, pp. 263–281, (1989).

Zimmermann, G.G., et al., "Evaluation of Catheter/Guide wire steerability: in vitro comparison of fluoroscopic guidance with active MR–tracking in an open 0.5R MR–system", Proceedings of the International Society for Magnetic Resonance in Medicine, Fifth Scientific Meeting and Exhibition, Vancourver, BC, Canada, vol. 3, p. 1930, (Apr. 12–18, 1997).

Bouvier, G., et al., "Direct Delivery of Medication into a Brain Tumor through Multiple Chronically Implanted Catheters", Neurosurgery, 20, No. 2, 286–291, (1987).

Chandler, W.F., et al., "Use of Implantable Pump Systems for Intraarterial, Intraventricular and Intratumoral Treatment of Malignant Brain Tumors", Ann. N.Y. Acad. Sci., 531, 206–212, (1988).

Gillies, G.T., et al., "Magnetic manipulation instrumentation for medical physics research", Rev. Sci. Instrum., 65(3), 533–562, (1994).

Hajnal, J.V., et al., "MR Imaging of Anisotropically Restricted Diffusion of Water in the Nervous System: Technical, Anatomic, and Pathologic Considerations", J. of Computer Assisted Tomography, 15(1), 1–18, ((1991).

Hurst, G.C., et al., "Intravascular (Catheter) NMR Receiver Probe: Preliminary Design Analysis and Application to Canine Iliofermoral Imaging", Mag. Res. Med., 24, 343–357, (1992).

Johnston, J., et al., "Shiley Infusaid Pump Technology", Ann. N.Y. Acad. Sci., 531, 57–65 (1988).

Kucharczyk, J., et al., "Differential effects of brain lesions on thirst induced by the administration of angiotensin–II ot the preoptic region, subfornical organ and anterior third ventricle", Brain Res., 108, 327–337, (1976).

Moseley, M.E., et al., "Magnetic resonance imaging of diffusion and perfusion", Top Mag. Reson. Imaging, 3(3), 50–67, (1991).

Schmitt, F.O., "Molecular Regulators of Brain Function: A New View", Neuroscience, 13, 991–1001, (1984).

Sendelbeck, S.L., et al., "Spatial Distribution of Dopamine, Methotrexate and Antipyrine During Continuous Intracerebral Microperfusion", Brain Res., 328, 251–258, (1985).

Swanson, L.W., et al., "Autoradiographic Evidence for Pathways from the Medial Preoptic Area to the Midbrain Involved in the Drinking Response to Angiotensin II", J. of Comparative Neurology, 178, No. 4, 645–659, (1978).

Wimberger, D.M., et al., "Identification of "Premyelination" by Diffusion–Weighted MRI", J. of Computer Assisted Tomography, 19(1), 28–33, (1995).

METHOD AND APPARATUS FOR USE WITH MR IMAGING

BACKGROUND OF THE INVENTION

1. Field of the Invention

This invention relates to the design, construction, and use of magnetic resonance (MR) imaging to identify areas within a patient where changes in a molecular environment are occurring, as from chemical concentration changes effected by medical procedures. The invention also describes a drug delivery device for targeted drug delivery into a patient using magnetic resonance (MR) imaging combined with conventional catheter placement techniques, particularly including neurosurgical or neuroradiologic techniques used in intracranial drug delivery.

2. Background of the Art

Although endoscopic, arthroscopic, and endovascular therapies have produced significant advances in healthcare, the diagnostic accuracy and clinical utility of these procedures is ultimately "surface limited" by what the surgeon can see through the device itself or otherwise visualize during the course of the procedure. Magnetic Resonance (MR) imaging, by comparison, overcomes this limitation by enabling the surgeon to noninvasively visualize tissue planes beyond the surface of the tissue under direct evaluation. Moreover, MR imaging enables differentiation of normal from abnormal tissues, and can display critical structures such as blood vessels in three dimensions. Thus, high-speed MR-guided therapy offers an improved opportunity to maximize the benefits of minimally invasive procedures. Prototype high-speed MR imagers which permit continuous real-time visualization of tissues during surgical and endovascular procedures have already been developed. Recent publications in the medical literature have described a number of MR-guided interventions including needle biopsies, interstitial laser therapy, interstitial cryotherapy and interstitial focused ultrasound surgery.

The standard current procedure for drug treatment of various focal neurological disorders, neurovascular diseases, and neurodegenerative processes requires neurosurgeons or interventional neuroradiologists to deliver drug agents by catheters or other tubular devices directed into the cerebrovascular or cerebroventricular circulation, or by direct injection of the drug agent, or cells which biosynthesize the drug agent, into targeted intracranial tissue locations. The blood-brain barrier and blood-cerebrospinal fluid barrier almost entirely exclude large molecules like proteins, and control entry of smaller molecules. Small molecules (<200 daltons) which are lipid-soluble, not bound to plasma proteins, and minimally ionized, such as nicotine, ethanol, and some chemotherapeutic agents, readily enter the brain. Water soluble molecules cross the barriers poorly or not at all. Delivery of a drug into a ventricle bypasses the blood-brain barrier, and allows for a wide distribution of the drug in the brain ventricles, cisterns, and spaces due to the normal flow pathways of cerebrospinal fluid in the brain. However, following intracerebroventricular injection, many therapeutic drug agents, particularly large-molecular weight hydrophobic drugs, fail to reach their target receptors in brain parenchyma because of metabolic inactivation and inability to diffuse into brain tissues, which may be up to 18 mm from a cerebrospinal fluid surface.

To optimize a drug's therapeutic efficacy, it should be delivered to its target tissue at the appropriate concentration. A number of studies reported in the medical literature, for example, Schmitt, Neuroscience, 13, 1984, pp. 991–1001, have shown that numerous classes of biologically active drugs, such as peptides, biogenic amines, and enkephalins have specific receptor complexes localized at particular cell regions of the brain. Placing a drug delivery device directly into brain tissue thus has the notable advantage of initially localizing the injected drug within a specific brain region containing receptors for that drug agent. Targeted drug delivery directly into tissues also reduces drug dilution, metabolism and excretion, thereby significantly improving drug efficacy, while at the same time it minimizes systemic side-effects.

An important issue in targeted drug delivery is the accuracy of the navigational process used to direct the movement of the drug delivery device. Magnetic resonance imaging will likely play an increasingly important role in optimizing drug treatment of neurological disorders. One type of MR unit designed for image-guided therapy is arranged in a "double-donut" configuration, in which the imaging coil is split axially into two components. Imaging studies are performed with this system with the surgeon standing in the axial gap of the magnet and carrying out procedures on the patient. A second type of high-speed MR imaging system combines high-resolution MR imaging with conventional X-ray fluoroscopy and digital subtraction angiography (DSA) capability in a single hybrid unit. Both of these new generations of MR scanners provide frequently updated images of the anatomical structures of interest. This real-time imaging capability makes it possible to use high-speed MR imaging to direct the movement of catheters and other drug delivery vehicles to specific tissue locations, and thereby observe the effects of specific interventional procedures.

A prerequisite for MRI-guided drug delivery into the brain parenchyma, cerebral fluid compartments, or cerebral vasculature is the availability of suitable access devices. U.S. Pat. No. 5,571,089 to Crocker et al. and U.S. Pat. No. 5,514,092 to Forman et al. disclose endovascular drug delivery and dilatation drug delivery catheters which can simultaneously dilate and deliver medication to a vascular site of stenosis. U.S. Pat. No. 5,171,217 to March describes the delivery of several specific compounds through direct injection of microcapsules or microparticles using multiple-lumen catheters, such as disclosed by Wolinsky in U.S. Pat. No. 4,824,436. U.S. Pat. No. 5,580,575 to Unger et al. discloses a method of administering drugs using gas-filled liposomes comprising a therapeutic compound, and inducing the rupture of the liposomes with ultrasound energy. U.S. Pat. No. 5,017,566 to Bodor discloses redox chemical systems for brain-targeted drug delivery of various hormones, neurotransmitters, and drugs through the intact blood-brain barrier. U.S. Pat. No. 5,226,902 to Bae et al. and U.S. Pat. No. 4,973,304 to Graham et al. disclose drug delivery devices, in which biologically active materials present within a reversibly permeable hydrogel compartment can be delivered into tissues by various endogenous and exogenous stimuli. U.S. Pat. No. 5,167,625 to Jacobsen et al. discloses an implantable drug delivery system utilizing multiple drug compartments which are activated by an electrical circuit. U.S. Pat. No. 4,941,874 to Sandow et al. discloses a device for the injection of implants, including drug implants that may used in the treatment of diseases. U.S. Pat. Nos. 4,892,538, 4,892,538, 5,106,627, 5,487,739 and 5,607,418 to Aebischer et al. disclose implantable drug therapy systems for local delivery of drugs, cells and neurotransmitters into the brain, spinal cord, and other tissues using delivery devices with a semipermeable membrane disposed at the distal end. U.S. Pat. No. 5,120,322 to Davis et al. describes the process of coating the surface layer of a stent or shunt with lathyrogenic agent to inhibit scar formation during reparative tissue formation, thereby extending exposure to the drug agent. U.S. Pat. No. 4,807,620 to Strul and 5,087,256 to Taylor are examples of catheter-based devices which convert electromagnetic Rf energy to thermal energy. Technology practiced by STS Biopolymers (Henrietta, N.Y.) allows incorporation of pharmaceutical agents into thin surface coatings during or after product manufacture. The invention disclosed by STS Biopolymers allows for the drugs to diffuse out of the coating at a controlled rate, thereby maintaining therapeutic drug levels at the coating surface while minimizing systemic concentrations. The coating can incorporate natural or synthetic materials that act as antibiotics, anticancer agents, and antithrombotics, according to the issued patent. U.S. Pat. No. 5,573,668 to Grosh et al. discloses a microporous drug delivery membrane based on an extremely thin hydrophilic shell. U.S. Pat. No. 5,569,197 to Helmus et al. discloses a drug device guidewire formed as a hollow tube suitable for drug infusion in thrombolytic and other intraluminal procedures.

A number of articles published in the medical literature, for example, Chandler et al., Ann. N.Y. Acad. Sci., 531, 1988, pp. 206–212, Bouvier et al., Neurosurgery 20(2), 1987, pp. 286–291, Johnston et al., Ann. N.Y. Acad. Sci., 531, 1988, pp. 57–67, and Sendelbeck et al., Brain Res., 328, 1985, pp. 251–258 describe implantable pump systems designed for continuous or episodic delivery of therapeutic drugs into the central nervous system via systemic, intrathecal, intracerebroventricular, and intraparenchymal injection or infusion.

The patented inventions referenced above provide useful methods for introducing, delivering, or applying a drug agent to a specific target tissue, but each invention also has inherent problems. For example, some catheter systems which provide endovascular drug delivery require temporary blocking of a segment of the vessel, thereby transiently disrupting brain perfusion. Microencapsulated coatings on catheters permit longer exposure of the tissue to the drug agent, but the physical limitations imposed by microcapsules restrict the volume and concentration of drug that can be effectively applied to any tissue area. Exposed coatings on catheters which contain drug agents usually require some type of sheath that must be removed from the catheter before the drug can be released from the coating. The sheath and any catheter components required to physically manipulate the sheath greatly increase the profile of the catheter, and thereby limit the variety of applications for which the drug delivery system can be employed. Furthermore, the binders or adhesives used in catheter coatings may themselves significantly dilute the concentration of the therapeutic agent. Finally, thermal and light energy required to melt and bond coatings such as macroaggregated albumin, to reduce tissue mass by ablation, and to inhibit restenosis by cytotoxic irradiation may also cause damage to blood vessels.

U.S. Pat. No. 5,470,307 to Lindall discloses a low-profile catheter system with an exposed coating containing a therapeutic drug agent, which can be selectively released at remote tissue site by activation of a photosensitive chemical linker. In the invention disclosed by Lindall, the linker is attached to the substrate via a complementary chemical group, which is functionalized to accept a complementary bond to the therapeutic drug agent. The drug agent is in turn bonded to a molecular lattice to accommodate a high molecular concentration per unit area and the inclusion of ancillary compounds such as markers or secondary emitters.

Although U.S. Pat. No. 5,470,307 to Lindall describes significant improvements over previous catheter-based drug delivery systems, there are nonetheless some problems. First, in common with other currently used endovascular access devices, such as catheters, microcatheters, and guidewires, the catheter tip is difficult to see on MRI because of inadequate contrast with respect to surrounding tissues and structures. This makes accurate localization difficult and degrades the quality of the diagnostic information obtained from the image. Also, the mere observation of the location of the catheter in the drug delivery system does not reliably or consistently identify the position, movement and/or efficient delivery of drugs provided through the system. Thus, one objective of this invention is to provide for an MR-compatible and visible device that significantly improves the efficacy and safety of drug delivery using MR guidance.

Any material that might be added to the structure of a pliable catheter to make it MR visible must not contribute significantly to the overall magnetic susceptibility of the catheter, or imaging artifacts could be introduced during the MR process. Moreover, forces might be applied to such a catheter by the superconducting magnetic manipulation coils of a nonlinear magnetic stereotaxis system which might be used in the practice of the present invention. In either case, the safety and efficacy of the procedure might be jeopardized, with resulting increased risk to the patient. Also, an MR-visible catheter must be made of material that is temporally stable and of low thrombolytic potential if it is to be left indwelling in either the parenchymal tissues or the cerebral vasculature. Examples of such biocompatible and MR-compatible materials which could be used to practice the invention include elastomeric hydrogel, nylon, teflon, polyamide, polyethylene, polypropylene, polysulfone, ceramics, cermets steatite, carbon fiber composites, silicon nitride, and zirconia, plexiglass, and poly-ether-ether-ketone.

It is also important that drug delivery devices used under MR guidance are MR-compatible in both static and time-varying magnetic fields. Although the mechanical effects of the magnetic field on ferromagnetic devices present the greatest danger to patients through possible unintended movement of the devices, tissue and device heating may also result from radio-frequency power deposition in electrically conductive material located within the imaging volume. Consequently, all cables, wires, and devices positioned within the MR imager must be made of materials that have properties that make them compatible with their use in human tissues during MR imaging procedures. Many materials with acceptable MR-compatibility, such as ceramics, composites and thermoplastic polymers, are electrical insulators and do not produce artifacts or safety hazards associated with applied electric fields. Some metallic materials, such as copper, brass, magnesium and aluminum are also generally MR-compatible, viz. large masses of these materials can be accommodated within the imaging region without significant image degradation.

Guidewires for the catheter or drug delivery system are usually made of radiopaque material so that their precise location can be identified during a surgical procedure through fluoroscopic viewing. Exemplary of guidewires used under X-ray viewing is the guidewire disclosed by LeVeen, U.S. Pat. No. 4,448,195, in which a radiopaque wire can be identified on fluoroscopic images by metered bands placed at predetermined locations. The U.S. Pat. No. 4,922,924, awarded to Gambale et al. discloses a bifilar arrangement whereby radiopaque and radiotransparent filaments are wrapped on a mandril to form a bifilar coil which provides radiopaque and radiotransparent areas on the guide wire. U.S. Pat. No. 5,375,596 to Twiss et al. discloses a method for locating catheters and other tubular medical devices implanted in the human body using an integrated system of wire transmitters and receivers. U.S. Pat. No. 4,572,198 to Codrington also provides for conductive elements, such as electrode wires, for systematically disturbing the magnetic field in a defined portion of a catheter to yield increased MR visibility of that region of the catheter. However, the presence of conductive elements in the catheter also introduces increased electronic noise and the possibility of Ohmic heating, and these factors have the overall effect of degrading the quality of the MR image and raising concerns about patient safety. Thus, in all of these examples of implantable medical probes, the presence of MR-incompatible wire materials causes large imaging artifacts. The lack of clinically adequate MR visibility and/or imaging artifact contamination caused by the device is also a problem for most commercially available catheters, microcatheters and shunts.

MRI enables image-guided placement of a catheter or other drug delivery device at targeted intracranial loci. High-resolution visual images denoting the actual position of the drug delivery device within the brain would be extremely useful to the clinician in maximizing the safety and efficacy of the procedure. Drug delivery devices, such as catheters, that are both MR-visible and radio-opaque could be monitored by both X-ray fluoroscopy and MR imaging, thus making intra-operative verification of catheter location possible.

Initial attempts to position and visualize endovascular devices in MR imaging were based on passive susceptibility artifacts produced by the device when exposed to the MR field. Magnetic susceptibility is a quantitative measure of a material's tendency to interact with and distort an applied magnetic field. U.S. Pat. No. 4,827,931, to Longmore and U.S. Pat. Nos. 5,154,179 and 4,989,608 to Ratner disclose the incorporation of paramagnetic material into endovascular devices to make the devices visible under MR imaging. U.S. Pat. No. 5,211,166 to Sepponen similarly discloses the use of surface impregnation of various "relaxants", including paramagnetic materials and nitrogen radicals, onto surgical instruments to enable their MR identification. However, these patents do not provide for artifact-free MR visibility in the presence of rapidly alternating magnetic fields, such as would be produced during echo-planar MR imaging pulse sequences used in real-time MR guidance of intracranial drug delivery procedures. Nor do these patents teach a method for monitoring with MR-visible catheters the outcomes of therapeutic interventions, such as, for example, drug delivery into brain tissues, cerebral ventricles, or subarachnoid space. Ultrafast imaging sequences generally have significantly lower spatial resolution than conventional spin-echo sequences. Image distortion may include general signal loss, regional signal loss, general signal enhancement, regional signal enhancement, and increased background noise. The magnetic susceptibility artifact produced by the device should be small enough not to obscure surrounding anatomy, or mask low-threshold physiological events that have an MR signature, and thereby compromise the physician's ability to perform the intervention. These relationships will be in part dependent upon the combined or comparative properties of the device, the particular drug, and the surrounding environment (e.g., tissue).

An improved method for passive MR visualization of implantable medical devices has recently been disclosed by Werne (Ser. No. 08/554,446) ITI Medical Technologies (Application Pending). This invention minimizes MR susceptibility artifacts, and controls eddy currents in the electromagnetic scattering environment, so that a bright "halo" artifact is created to outline the device in its approximately true size, shape, and position. In the method of the invention disclosed by ITI, an ultra thin coating of conductive material comprising 1–10% of the theoretical skin depth of the material being imaged—typically about 250,000 angstroms—is applied. By using a coating of 2,000–25,000 angstroms thickness, ITI has found that the susceptibility artifact due to the metal is negligible due to the low material mass. At the same time, the eddy currents are limited due to the ultra-thin conductor coating on the device. A similar method employing a nitinol wire with Teflon coat in combination with extremely thin wires of a stainless steel alloy included between the nitinol wire and Teflon coat, has recently been reported in the medical literature by Frahm et al., Proc. ISMRM, 3, 1997, p. 1931.

Exemplary of methods for active MR visualization of implanted medical devices is U.S. Pat. No. 5,211,165 to Dumoulin et al., which discloses an MR tracking system for a catheter based on transmit/receive microcoils positioned near the end of the catheter by which the position of the device can be tracked and localized. Applications of such catheter-based devices in endovascular and endoscopic imaging have been described in the medical literature, for example, Hurst et al., Mag. Res. Med., 24, 1992, pp. 343–357, Kantor et al., Circ. Res., 55, 1984, pp. 55–60; Kandarpa et al., Radiology, 181, 1991, pp. 99; Bomert et al., Proc. ISMRM, 3, 1997, p. 1925; Coutts et al., Proc. ISMRM, 3, 1997, p. 1924; Wendt et al., Proc, ISMRM, 3, 1997, p. 1926; Langsaeter et al., Proc. ISMRM, 3, 1997, p. 1929; Zimmerman et al., Proc. ISMRM, 3, 1997, p. 1930; and, Ladd et al., Proc. ISMRM, 3, 1997, p. 1937.

In the treatment of neurological diseases and disorders, targeted drug delivery can significantly improve therapeutic efficacy, while minimizing systemic side-effects of the drug therapy. Image-guided placement of the tip of a drug delivery catheter directly into specific regions of the brain can initially produce maximal drug concentration close to the loci of tissue receptors following injection of the drug. At the same time, the limited distribution of drug injected from a single catheter tip presents other problems. For example, the volume flow rate of drug delivery must be very low in order to avoid indiscriminate damage to brain cells and nerve fibers. Delivery of a drug from a single point source also limits the distribution of the drug by decreasing the effective radius of penetration of the drug agent into the surrounding tissue receptor population. Another aspect of this invention is therefore to overcome these inherent limitations of single point source drug delivery by devising a multi-lumen catheter with multiple drug release sources which effectively disperse therapeutic drug agents over a brain region containing receptors for the drug, or over an anatomically extensive area of brain pathology.

SUMMARY OF THE INVENTION

Magnetic Resonance Imaging (MRI) is used in combination with 1) an MR observable delivery device or 2) an MR observable medical device which can alter a water based molecular environment by performed medical operations, the delivery device or medical device being used in the presence of MR observable (in water, body fluid or tissue) compound(s) or composition(s). MRI images are viewed with respect to a molecular environment to determine the position of the delivery or medical device (hereinafter collectively referred to as the "delivery device" unless otherwise specifically identified) and changes in the environment where the delivery device is present as an indication of changes in the molecular environment. As the delivery of material from the delivery device is the most significant event within the molecular environment in the vicinity of the delivery area, the changes in the molecular environment are attributable to the delivery of the MR observable compounds or compositions. Changes in signal intensity within the MR images reflect the changes in the molecular environment and therefore track the location of delivered materials, and are indicative of delivery rates and delivery volumes in viewable locations. With the medical device, chemical composition within the molecular environment may also be altered as by the removal of deposits of certain materials into the liquid (water) environment, where those materials can alter the MR response. Some materials which may be removed by medical procedures will not affect the MR response, such as calcium, but fatty materials may. Additionally, medical treatments which stimulate natural activities of chemical producing systems (e.g., the glands, organs and cells of the body which generate chemicals such as enzymes and other chemicals with specific biological activity [e.g., dopamine, insulin, etc.] can be viewed under direct MR observation and any changes in chemical synthetic activity and/or delivery can be seen because of molecular environment changes which occur upon increased synthetic activity.

One recently established method of reading the data obtained from the MR imaging is technically founded upon existing knowledge of Apparent Diffusion Coefficients (ADC) in particular regions of the body. There is significant published literature with respect to ADC values for specific tissues in various parts of animals, including various tissues of humans (e.g., Joseph V. Hajnal, Mark Doran, et al., "MR Imaging of Anisotropically Restricted Diffusion of Water in the Nervous System: Technical, Anatomic, and Pathological Considerations," *Journal of Computer Assisted Tomography*, 15(1): 1–18, January/February, 1991, pp. 1–18). It is also well established in the literature that loss of tissue structure through disease results in a decrease of the ADC, as the tissue becomes more like a homogeneous suspension. Clinical observations of changes in diffusion behavior have been made in various tissue cancers, multiple sclerosis, in stroke, where the reduction in diffusion precedes the increase in T2, and in epilepsy. Thus, ADC values are specific for specific types of tissues. Accordingly, as different drugs/chemicals are introduced into a tissue volume under MR observation, the ADC resulting from each drug/chemical interaction can be observed and the change in the ADC can be determined for that drug/chemical interaction with that particular tissue/drug environment.

While the ADC is the preferred means within the present invention of mapping the delivery of drug in tissue, other embodiments of the invention allow for additional tissue contrast parameters to track the delivery of a drug into tissue. In other words, the delivery of a drug into tissue will cause other MRI-observable changes which can be mapped (as is done for ADC) and which can be used to spatially track the delivery and extent of a drug into a tissue. While some of these observations may be larger in magnitude than others, any of the effects can be used as a tracking mechanism.

The tissue contrast changes apparent on an MR image can arise from ADC, from alterations in the B0 magnetic field (often referred to as magnetic susceptibility or ΔB0 produced by the presence of a substance in said tissue), from alterations in local tissue T1 relaxation times, from local T2 relaxation times, from T2* relaxation times (which can be created by susceptibility differences), from the magnetization transfer coefficients (MTC is an effect produced by local communication between free water protons and those of nearby macromolecular structures), from the ADC anisotropy observed in oriented matter, and also from local differences in temperature which will affect in varying degrees all of the included tissue contrast parameters. In addition, the delivery of drug can also be tracked from magnetic filed frequency shifts caused by the drug or arising from agents added with unique frequency shifts from those of the local protons (such as that created from F-19 or fluorine-19 agents found in or added to the drug).

MR imaging of the alterations in the B0 magnetic field (also known as imaging of the local magnetic susceptibility) can reveal the spatial distribution of a drug from the interaction of the drug with the otherwise homogeneous magnetic field found in MRI. To enhance the alterations in the magnetic field B0 caused by the drug, small amounts of a B0-altering added agents can be added to the drug during delivery. This can include iron oxide particles, or materials comprising lanthanide-, manganese-, and iron-chelates. In addition, vehicles containing differing gases (N2, O2, CO2) will also alter the local magnetic field and thus produce a magnetic susceptibility effect which can be imaged.

The invention includes a device and a method for MR-guided targeted drug delivery into a patient, such as intracranial drug delivery, intraspinal drug delivery, intrarenal drug delivery, intracardial drug delivery, etc. The MR-visible drug delivery device is guided to target entrance points to the patient such as periventricular, intracerebroventricular, subarachnoid, or intraparenchymal tissues magnetic resonance imaging, or conventional methods of neurosurgical or neuroradiologic catheter manipulation. The drug delivery device has a linearly arranged array of radiopaque and MR-visible markers disposed at its distal end to provide easily identifiable reference points for trackability and localization under susceptibility MR imaging and X-ray fluoroscopy guidance. Additionally, active MR visualization of the drug delivery device is achieved by means of RF microcoils positioned along the distal axis of the device. MR visibility can be variably adjustable based on requirements related to degree of signal intensity change for device localization and positioning, enhancement along the shaft of the device, enhancement around the body of the device, visibility of the proximal and distal ends of the device, degree of increased background noise associated with device movement, and other factors which either increase or suppress background noise associated with the device. Since the tip of the drug delivery device can be seen on MR and X-ray images and thus localized within the brain, the multiple point source locations of drug delivery are therefore known and can be seen relative to the tip or the shaft of the device.

Targeted delivery of drug agents is performed utilizing MR-compatible pumps connected to variable-length concentric MR-visible dialysis probes each with a variable molecular weight cut-off membrane, or by another MR-compatible infusion device which injects or infuses a diagnostic or therapeutic drug solution. Imaging of the injected or infused drug agent is performed by MR diffusion mapping using the RF microcoils attached to the distal shaft of the injection device, or by imaging an MR-visible contrast agent that is injected or infused through the walls of the dialysis fiber into the brain. The delivery and distribution kinetics of injections or infusions of drug agents at rates between 1 ul/min to 1000 ul/min are monitored quantitatively and non-invasively using real-time contrast-enhanced magnetic susceptibility MR imaging combined with water proton directional diffusion MR imaging.

One aspect of the present invention is to provide a non-invasive, radiation-free imaging system for tracking a drug delivery device to a target intracranial location.

Another aspect of the present invention is to provide an imaging system for visualizing the distal tip of the drug delivery device at the target intracranial location.

A third aspect of this invention is to provide for an MR-compatible and visible device that significantly improves the efficacy and safety of intracranial drug delivery using MR guidance.

A fourth aspect of the present invention is to provide for interactive MR imaging of injected or infused MR-visible drug agents superimposed upon diagnostic MR images of the local intracranial anatomy.

A fifth aspect of the present invention is provide an MR imaging method for quantitative monitoring of the spatial distribution kinetics of a drug agent injected or infused from a drug delivery device into the central nervous system, in order to determine the efficacy of drug delivery at various intracranial target sites.

A sixth aspect of the present invention is to provide an MR imaging method to evaluate how the spatial distribution kinetics of a drug agent injected or infused from a drug delivery device into the central nervous system is influenced by infusion pressure, flow rate, tissue swelling and other material properties of the brain, and by the physicochemical nature of the drug agent infused.

DETAILED DESCRIPTION OF THE INVENTION

Figure 1:
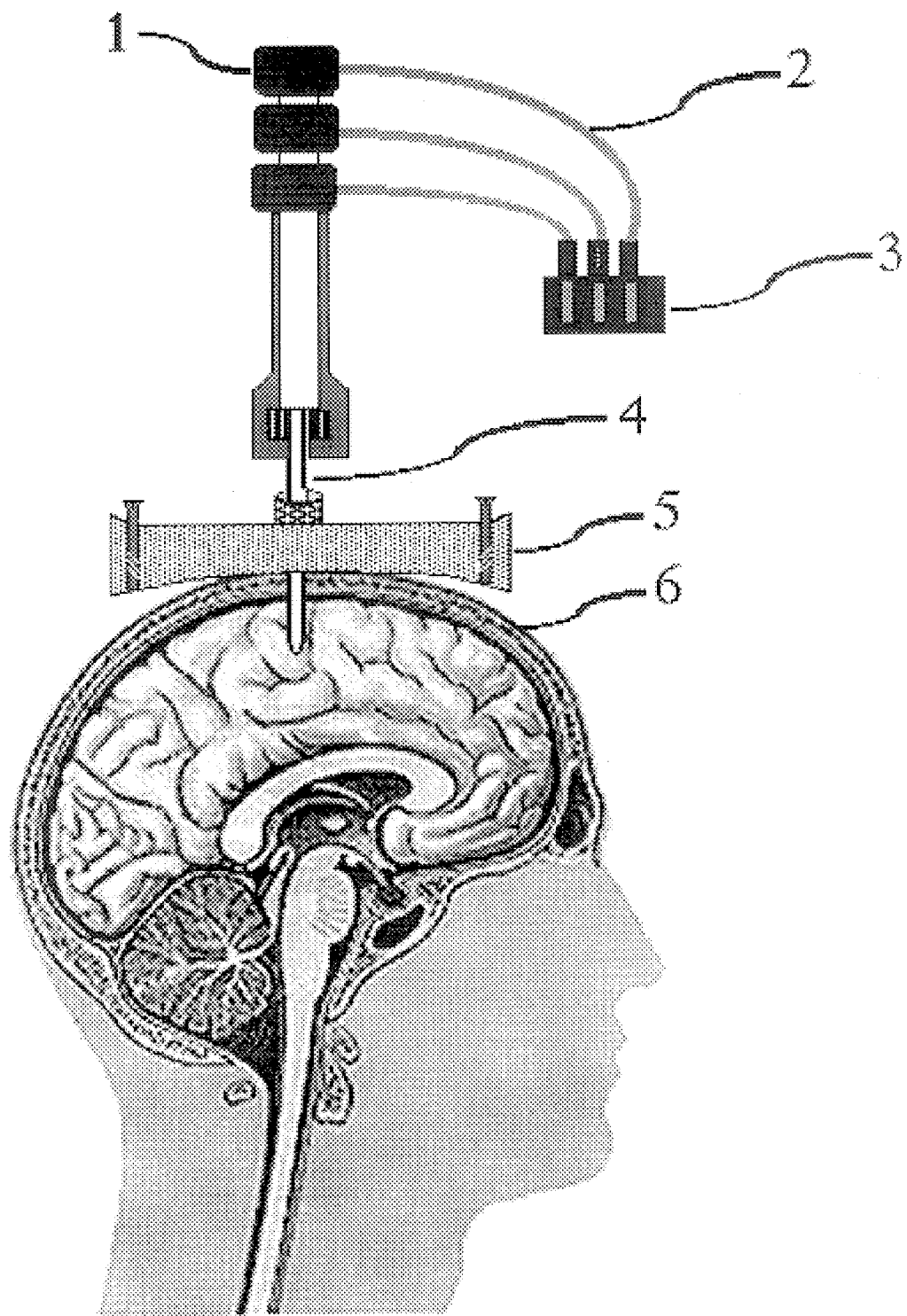
FIG. 1 is a schematic of the drug delivery device illustrating an exemplary method of practicing the present invention.

One of the significant difficulties with delivery of materials such as drugs, hormones, or neurotransmitters to living tissue is assuring that the materials are delivered to the target receptor location in the intended amount. Many materials which are delivered to a patient, even though beneficial in the treatment of a specific condition, may be moderately or even strongly noxious or damaging to healthy tissue. It is therefore one object of conventional materials application treatment to maximize dosage to a desired location and to minimize dosage to locations which do not require the delivery of the material. Additionally, newer medical treatments may include procedures which remove unwanted deposits of materials with an expectation that the removal will be assisted by physical removal (by a withdrawal system) or natural bodily function removal (e.g., the circulatory system), or which may attempt to stimulate the body to produce natural chemicals (of which a patient may be deficient) at an increased rate (e.g., electrical stimulation to increase the production of dopamine). Because these procedures are usually highly invasive, it would be extremely desirable to have a real time indication of immediate, transient and persistent effectiveness of the procedure. Where undesired deposits or collections of materials are being dispersed, it would be desirable to visualize the actual movement of materials to assist in collecting them (e.g., through catheters) or tracking them to assure that they are not again depositing or collecting (as in intravenous or cerebrospinal fluid blockage), or moving in segments which are too large and could cause blockage in other parts of the body as they are carried about.

Unfortunately, with in vivo delivery of materials, particularly extremely small doses in small volumes delivered by small instrumentation into tissue regions protected by the blood-brain barrier, or the brain-cerebrospinal fluid barrier, or into visually inaccessible areas, it has not been possible to observe real time distribution of the material delivery, or the dispersion or distribution of the material at the injection or infusion site within the tissue. Where even small variations or miscalculations about the location of the target sight and the delivery device can significantly affect the delivery of material and the effectiveness of the delivered material, real time observation of the material delivery is even more critical than in topical or gross (e.g., massive systemic injection) delivery events. There has been no truly effective observation system for such delivery prior to the present invention.

The basic operation of the present invention therefor involves the initial MR imaging observation of a molecular environment of a patient (e.g., a particular area or region of a patient, such as tissue, particularly such tissue as that present in organs or systems of animal bodies and especially the human body, including, but not limited to the intracranial compartment and the various anatomic regions of the brain, including the cerebral ventricles, cisterns, epidural and subdural spaces, sinuses, and blood vessels, the spinal cord, including disks, nerves and associated vascular system, the heart and the coronary vascular circulation, liver and the hepatic vascular circulation, kidney and the renal vascular circulation, spleen and the splenic vascular system, gastrointestinal system, special senses, including the visual system, auditory system, and olfactory system endocrine system including the pituitary gland, thyroid gland, adrenal gland, testes, and ovaries, with observation of an MR image signal intensity at a given time and/or state (e.g., prior to material introduction or at some defined stage of material diffusion into the molecular environment. In an example of the method of the invention, the distribution of the material in the tissue is determined by releasing an amount of the material through a drug delivery device positioned in the tissue, allowing the material to diffuse in the tissue, and analyzing the resulting MR signal intensity. On a continual basis or at some subsequent time interval later (e.g., a pulsed interval, preselected interval, random interval, frequent or sporadic intervals), the MR image of the molecular state within the same general area is observed. Changes in the characteristics, properties or quality of the image, such as the image signal intensity within the area are presumptively (and in most cases definitively) the result of the introduction of material into the original molecular environment and alteration of the MR response for regions of the environment where delivered material concentration has changed. By repeating observation of the MR image signal intensity within an area at least once (e.g., first taking the initial observation at a material concentration state at a time TI, and at least one subsequent observation of MRI-observable changes such as in the signal intensity qualities at a time $T_2$), the change in MR image signal intensity qualities can be related to the change in material concentration between times $T_1$ and $T_2$, whether that change is from a starting point of zero concentration or from an existing concentration level. The observations therefore relate to the actual delivery of material into the molecular environment in an observable, and to some lesser degree, quantifiable manner.

The change in the signal, e.g., the change in the amplitude of the MR signal in the visible image may be altered by:

a) a change in the apparent diffusion coefficient (ADC) of tissue water protons;

b) a change in tissue magnetic susceptibility (BO);

c) a change in T1 tissue relaxivity (T1);

d) a change in T2 tissue relativity (T2);

e) a change in tissue magnetization transfer coefficients (MTC);

f) a change in tissue chemical shift frequency;

g) a change in tissue temperature; or h) a combination of any one or more of a)–g) alone or with other effects.

The MR signal is dephased by the random motion of diffusing water molecules, and the presence of the delivered material locally affects the degree to which the amplitude of the signal is altered by the dephasing. If the amount of active ingredient to be delivered is quite small, or the effect of that material on the alteration of the amplitude is minimal, the delivered material may be associated with a larger amount of a second material or another more MR signal responsive material, which are preferably selected on a basis of similarity in diffusion rates through like materials or at least comparable (mathematically relatable) diffusion rates. In this manner, using such a taggant material, the diffusion of the delivered material may be assumed to relate to the diffusion/delivery of the taggant material. Unlike other observational techniques, these taggant materials may be readily provided as non-toxic, inexpensive taggant materials since there is such a wide variety of materials which could be so used, and their only functional requirements would be diffusion rate and non-toxicity. Many dyes commonly used in medical procedures could be used for this purpose.

The availability of an MR-visible drug delivery device combined with MR-visible chemical or drug agents would make it possible to obtain near real-time information on drug delivery during interventional procedures in an intraoperative MR system, as well as for pre-operative and post-operative confirmation of the location of the drug delivery device. Medical and surgical applications would include vascular surgery and interventional radiology, cardiac surgery and cardiology, thoracic surgery and radiology, gastrointestinal surgery and radiology, obstetrics, gynecology, urology, orthopedics, neurosurgery and neurointerventional radiology, head & neck surgery and radiology, ENT surgery and radiology, and oncology. In addition to direct tissue injection, the method of the invention applies to drug delivery via intraluminal, intracavitary, laparoscopic, endoscopic, intravenous, intraarterial applications.

There is currently considerable interest in the therapeutic use of small ions as well as macromolecules in the treatment of various neurologic diseases. To be effective, such molecules must be able to reach target tissue receptors. Many molecules that are used in therapeutic drugs are large in size, for example, neuroleukin, a neuromodulator drug tested for treatment of amyotrophic lateral sclerosis is about 56 kDa, bethanechol chloride used in treatment of Alzheimer's Disease is about 196 kDa and nerve growth factor is about 13 kDa. While the importance of large molecular weight molecules in direct parenchymal drug therapy is growing, little is known about the time course and the spatial range of their actions, since dynamic visualization methods for studying macromolecular diffusion have not been available.

Diffusion of drug and/or water protons in a complex medium, such as a brain cell microenvironment, is influenced by numerous factors. Materials injected into the brain or spinal cord do not move unimpeded through the aggregations of neurons, glia, capillaries, and nerve fibers. The distribution of a drug volume in the brain cell microenvironment following injection directly into brain tissue is governed by a number of factors including the physicochemical characteristics of the drug, capillary uptake, metabolism, excretion, size of the extracellular space (the volume fraction), and geometry of the brain cell microenvironment (tortuosity). The degree to which each of these factors influences the distribution of a particular drug agent within the brain or spinal cord is an important determinant of the effectiveness of drug treatment of diseases of the central nervous system.

Despite the fact that the average spacing between brain cells may be no more than 20 nm, the mean free path of an ion at the typical ionic strength of the mammalian nervous system (about 0.15) is only about 0.01 nm. In ways similar to altering the local ADC of the water protons, presence and transport of a drug through a tissue will also alter the magnetic susceptibility, T1, T2, MTC, water proton diffusion anisotropy, chemical shift frequency, and temperature of the protons within each imaged voxel. This represents the distance traveled between collisions with other molecules. Almost all these collisions actually take place with water molecules since the concentration of water is 55 M. Thus ions intrinsic to the brain rarely encounter cell membranes and generally behave as though they were in a free medium. However, the diffusivity properties becomes much more complicated when the boundary has a complex geometry, or when macromolecular interactions involve exogenous solutions injected into tissues.

In complex media such as brain tissue, diffusion obeys Ficks Law, subject to two important modifications. First, the diffusion coefficient, D, is reduced by the square of the tortuosity factor to an apparent diffusion coefficient ADC*= D/tortuosity factor 2 because a diffusing material encounters membranous obstructions as it executes random movements between cells. Second, the source strength is divide by the volume fraction of the extracellular space so that a given quantity of released material becomes more concentrated than it would have been in a free medium.

In most media, tortuosity and volume fraction are essentially dimensionless factors which depend only on the geometrical constraints imposed by local structures. In brain tissue, however, a third factor, non-specific uptake, is present in the diffusion equation as a term, k', for loss of material across the cell membranes. In fact k' can be expressed as P (S)/volume fraction, where P is the membrane permeability and (S) is the volume average of the membrane surface area. Complex local boundary conditions imposed by cell membranes can thus be removed by averaging the local diffusion equations and boundary conditions over some characteristic volume of tissue a few micrometers in extent. Thus in the case where a substance is injected from a point source at a rate of q moles/sec in a free medium, the source term becomes q/tortuosity in a complex medium while the diffusion coefficient ADC is modified to be ADC/volume fraction 2 in the new equation, which is the apparent diffusion coefficient.

Knowledge of the properties of the brain extracellular microenvironment is thus essential to understanding the role of diffusion in delivering metabolic or therapeutic agents to brain or spinal cord cells. Diffusion has been determined employing radioactive or fluorescent tracers, in which the concentration profiles of the tracer are monitored over time, and its diffusivity is inferred from the data. Microscopic displacements can be seen with tracers on the scale of millimeters. Spatially resolved methods, such as infrared spectroscopy or Rayleigh scattering, have been used allowing resolution in the micrometer range. Such tracer techniques have been successfully applied in biological systems, such as the brain. However, because of the inherent invasiveness of using exogenous tracers, such techniques cannot be used in vivo with humans.

Techniques have also been developed for determining the diffusion characteristics of small molecules in local regions of the brain using radiotracers, microiontophoresis, or pressure microinjection combined with ion-selective microelectrodes. The applications of these methods to intracranial drug delivery have been described in the medical literature, for example, Lux et al., Exp. Brain Res., 17, 1973, pp. 190–205, Gardner-Medwin, Neurosci. Res. Progr. Bull., 1980, 18, pp. 208–226, Nicholson et al., J. Physiol., 1981, 321, pp. 225–257, Nicholson et al., Brain Res., 1979, 169, pp. 580–584. However, these techniques have several key limitations. First, these techniques provide a measurement at only a single point in the tissue so that spatial patterns of diffusion cannot be determined. Second, ion-selective microelectrodes can only be used with a few small ions. Third, since radiotracer techniques rely on postmortem counting of particles in fixed and sectioned tissues, they provide limited spatial resolution and no dynamic information.

Several previous studies have obtained estimates of the ADC of large fluorescent molecules from digitized images of fluorescent molecules as they diffused away from blood vessels. However, the complicated geometry of the source and inability to precisely characterize the emitted flux, substantially limit the clinical utility of the information. Similarly, new optical imaging methods, in which a uniform distribution of fluorescent tracer is first established in the sample and then a region is photobleached with a strong laser, has serious limitations because the laser beam can also damage the tissue area being imaged. Studies with optical fluorescence methods suggest that molecules as large as 70 kDa can pass through the brain extracellular microenvironment. Below some limit between 10 and 40 kDa, molecular diffusion is not restricted any more than with much smaller molecules. Similar constraints have been found for diffusion in the brain intracellular microenvironment, whereby all molecules diffuse at least three times slower than in aqueous solution, suggesting a similar tortuosity in the intracellular environment.

An integrative optical imaging technique disclosed by Tao and Nicholson, Biophysical J., 1993; 65, pp. 2277–2290 yields an apparent diffusion coefficient from digitized images, and enables precise determination of the diffusion characteristics of fluorescently labeled compounds of high molecular weight. The generalized equations disclosed by Nicholson and Tao have two nondimensional factors that incorporate the structure of the tissue into the imaging solution. The first factor, the tortuosity, accounts for the hindrance to extracellular diffusion that arises from the obstructions presented by cell membranes. The second structural factor is the volume fraction, which is defined as the ratio of the volume of the brain extracellular microenvironment to the total volume of tissue averaged over some small reference domain. The method disclosed by Nicholson and Tao ("Hindered diffusion of high molecular weight compounds in brain extracellular microenvironment measured with integrative optical imaging." Biophysical J. 1993; 65:2277–2290) does not, however, yield a direct measurement of the molecular distribution in a three-dimensional sample, and furthermore requires use of large fluorescent markers which are not suitable for repeated injections in human patients.

An alternative approach to measuring diffusivity of therapeutic drug injections is to monitor the diffusion process itself, i.e. the random motions of an ensemble of particles. Einstein showed that the diffusion coefficient measured in nonequilibrium concentration cell experiments is the same quantity that appears in the variance of the conditional probability distribution, $P(r/ro, t)$, the probability of finding a molecule at a position r at a time t, which was initially at a position ro. For free diffusion, this conditional probability distribution obeys the same diffusion relation. Thus, MR imaging parameters which reflect the differences in relative water proton-diffusion path lengths may serve to enable imaging differentiation between tissue water protons and protons in macromolecular solutions that are injected into brain tissues.

Molecular water-proton diffusion is caused by thermally induced random Brownian motion. As the protons continually collide with their microenvironments, their average random traveled pathlength <L>, along one direction (e.g. along the magnet-bore direction) is described according to Einstein as: $<L^2>=2TD$ where over an observation time of T (seconds) the displacement is expressed by a "diffusion coefficient, D" in $mm^2/s$ or $cm^2/s$. The diffusion process is continuous, so that the average displacement of any population of water protons increases with MR imaging time. However, the diffusion behavior of protons can be hindered by impermeable or semi-permeable barriers, such as cell membranes, and macromolecules, which may themselves contain populations of diffusing protons. For tissue water protons diffusing within a tissue matrix, the observed diffusion rate and direction will reflect the molecular and macromolecular barriers or hindrances that the diffusing protons encounter during their translational processes. One example of the application of this concept in human neurobiology is that myelinated nerve fibers in the brain and spinal cord preferentially dispose the diffusion of water protons along, rather than across, myelin tracts thereby giving rise to diffusional anisotropy MR imaging properties (Moseley et al., Mag. Res. Med., 19, 1991, pp. 321–326, Moseley et al., Topics Mag. Res. Med., 3, 1991, pp. 50–68).

Although noted for its effects on high-resolution, high-field MR spectra more than 25 years ago, molecular (water proton) diffusion has just recently been shown to have an important impact in clinical MR neuroimaging applications. While T1 and T2 relaxation times reflect frequency-dependent rotational and proton exchange processes, diffusion is caused solely by molecular or proton displacements or translations. Molecular size, shape, microenvironment, and temperature all influence the diffusion rate of molecules. Generally, larger molecules will translate (diffuse) more slowly than smaller molecules, such as water protons, and the differences in diffusion rates between different populations of molecules can be distinguished by signal intensity differences on diffusion-weighted MR images, particularly MR images which employ large diffusion gradients (b values). Thus, the measurable diffusion of smaller versus large molecules with MR imaging can be used as an in vivo tracer to probe the structural orientation of the tissues into which the drug agent has been injected. Advances in diffusion-weighted MR imaging have been made possible by major technical improvements in MR scanner hardware and software. High-speed MR echo-planar imaging now enables subsecond diffusion-sensitive imaging of water proton behavior in brain and spinal cord.

Thus, MR-visible molecules may exist in a variety of environments in brain tissue, which modify the way in which the molecules can move. First, the space in which the molecules can move may be small (e.g., intracellular) or large (e.g., an enlarged extracellular space). Second, the amount of dissolved compounds and proteins may alter the viscosity of the substance injected into the tissue. The random movement of the molecules is characterized by its diffusion coefficient ADC as the mean square distance moved for unrestricted isotropic (i.e. same in all directions) diffusion (for example a large sample of pure water). ADC is high in pure water, and lower by about a factor of 10 in tissue. As tissue becomes destroyed by disease processes, ADC is expected to rise toward its free water value. Diffusion-weighted imaging, in which field gradients are applied to attenuate the signal from rapidly diffusing water, shows increased image intensity in areas of low ADC. Similarly, the presence of a drug in tissue, or its transport through tissue extracellular, intercellular or intracellular microenvironments, will also alter the magnetic susceptibility, T1, T2, MTC, water proton diffusion anisotropy, chemical shift frequency, and temperature of protons within each imaged voxel.

The medical treatment and the medical device used in the practice of the present invention, even when a delivery device, may also be a diagnostic device rather than only a treatment device. For example, there are numerous diseases which alter the thickness of specific layers or coverings within the body, such as the myelin around nerves. The present invention provides a diagnostic tool to the degree that alterations in the thickness or existence of coatings such as myelin will alter the transport of chemical from one part of the body to another. Where, as in certain myelin deficiency diseases such as Multiple Sclerosis, the effect on the myelin is progressive and not uniform, the administration of chemicals into an area under MR imaging guidance according to the present invention can enable viewing of the variations in the rate of migration or transport of these observable chemicals to different areas of the myelinated nerve. The degree of advance of the disease can thus be observed, and it is possible to diagnose or even quantify the stage of the disease more acutely and comparatively within a given patient. According to that method, a chemical material would be introduced into the patient, and the relative movement of that chemical through supposedly similar structures in the area could be observed. Significant differences in penetration rates and/or concentrations of these chemicals through similar tissue material (e.g., the myelin) would be indicative of different properties (e.g., thickness, hydrophilicity, porosity, etc.) which would be symptomatic of a disease. The observation would therefore provide data that could support or prove a clinical diagnosis of a disease which is known to affect the specific properties observed.

Figure 2:
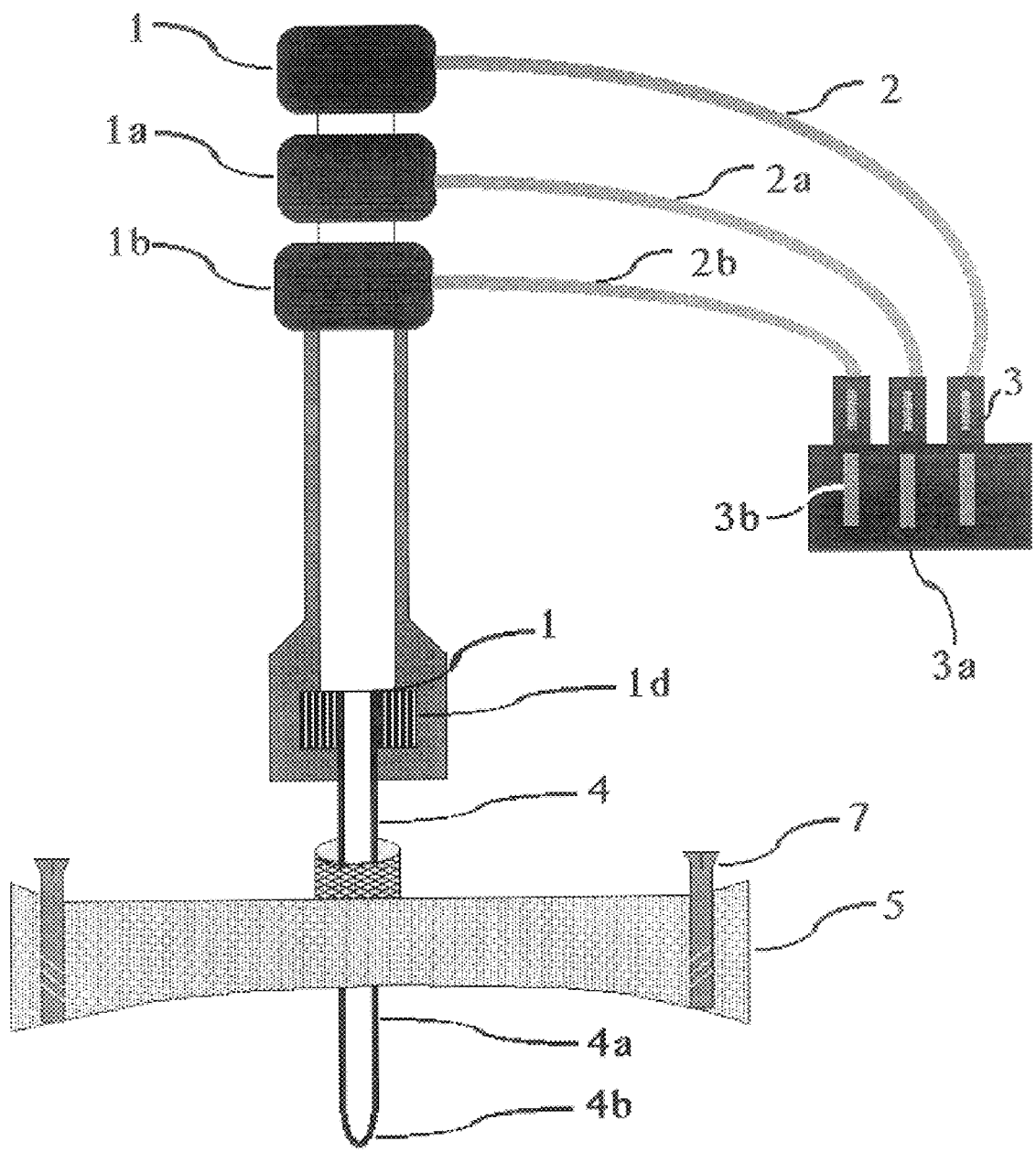
FIG. 2 is a cross-sectional view of the preferred embodiment of the drug delivery device, shown on a platform located above an anatomically targetted site in the brain. The view shows the disposition of a pump or reservoir containing the injectable material in relation to the other components of the device.

FIGS. 1 and 2 illustrate an MR-compatible drug delivery device made in accordance with the most preferred embodiment of the present invention. A variable-length concentric MR-visible multi-lumen catheter 4 is formed by extruding a tubular assembly with both porous 4$b$ and non-porous 4$a$ tubular components, The non-porous tubular component 4$a$ is made of MR-visible elastomeric hydrogel, various polymeric compositions including polyvinylchloride, polyacrylonitrile, polyvinylidene fluoride, polystyrene, polyurethane, and polyamides, or other similar low friction material intended to minimize abrasive damage to the brain during insertion. One or more of the tubing conduits 2, 2$a$, 2$b$ in the multi-lumen catheter are connected to a pump 3, 3$a$, 3$b$ or other temporary reservoir 1, 1$a$, 1$b$, which circulates a therapeutic drug solution or MR-sensitive contrast agent through a dialysis fiber into a target tissue or pathological lesion. The distal terminus of each porous tubular component 4$b$ has a dialysis probe 17 with a variable molecular weight cut-off membrane 18 which permits unimpeded movement of cerebrospinal fluid, small ions, and small molecular weight drugs, but is substantially impermeable to blockage by cellular material, said semipermeable membrane having a molecular weight exclusion of approximately 100–200 kD. The dialysis membranes can be made of regenerated cellulose hollow fiber tubing, as well as various polymeric compositions including polyvinylchloride, polyacrylonitrile, polyvinylidene fluoride, polystyrene, polyurethane, polyamides, cellulose acetates and nitrates, polymethylmethacrylate, polysulfones, polyacrylates, and derivatives, copolymers and mixtures thereof.

The inlet tubing of the dialysis probe is connected to a microinjection pump 3 or reservoir 1 providing a flow of 0.1–10 $\mu$l/minute of drug solution or sterile Ringer's solution perfusing the inside of the probe. The outlet tubing 2$a$ is connected to a section of plastic tubing leading to a collection vial 3$a$. Regenerated cellulose hollow fiber dialysis tubing is cemented into the distal end of the plastic tubing with clear epoxy or other MR-compatible bonding material. The dialysis fiber (Spectra/Or; Spectrum Medical) or other similar commercially available semi-permeable membrane has a nominal molecular weight cut-off of 100–200 kD, an i.d. (interior diameter) of 5–50 µm, and a membrane length of 1–10 mm.

Figure 3A:
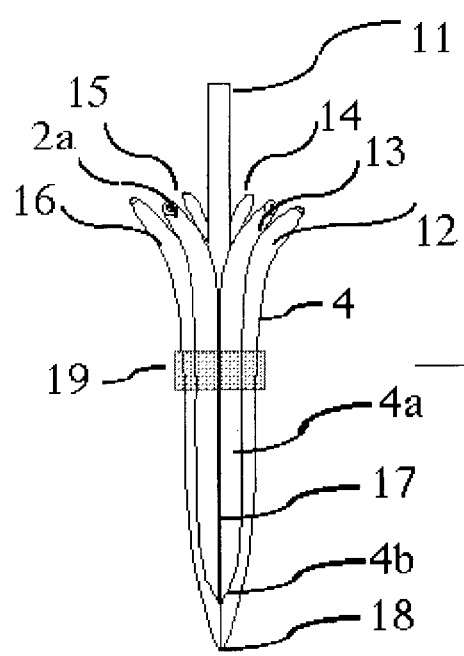
FIGS. 3A and 3B illustrate the preferred arrangement of the individual delivery catheters within the assembly of the multi-lumen delivery device.

With further reference to FIGS. 1–3 of the drawings, the outlet tubing 2a is incorporated into the probe into the dialysis chamber 1 via a small perforation in the inlet tubing. The entire upper portion of the assembly, including the junction between the inlet tubing and plastic cannula, is sealed with epoxy. The outer tubing consists of 5–10 cm length of flexible fused silica tubing (Polymicro Technologies). These probes are inexpensive and easy to construct, and the small o.d. minimizes the tissue damage. The concentric design makes it simple to implant the probe into different intracranial locations.

Figure 4:
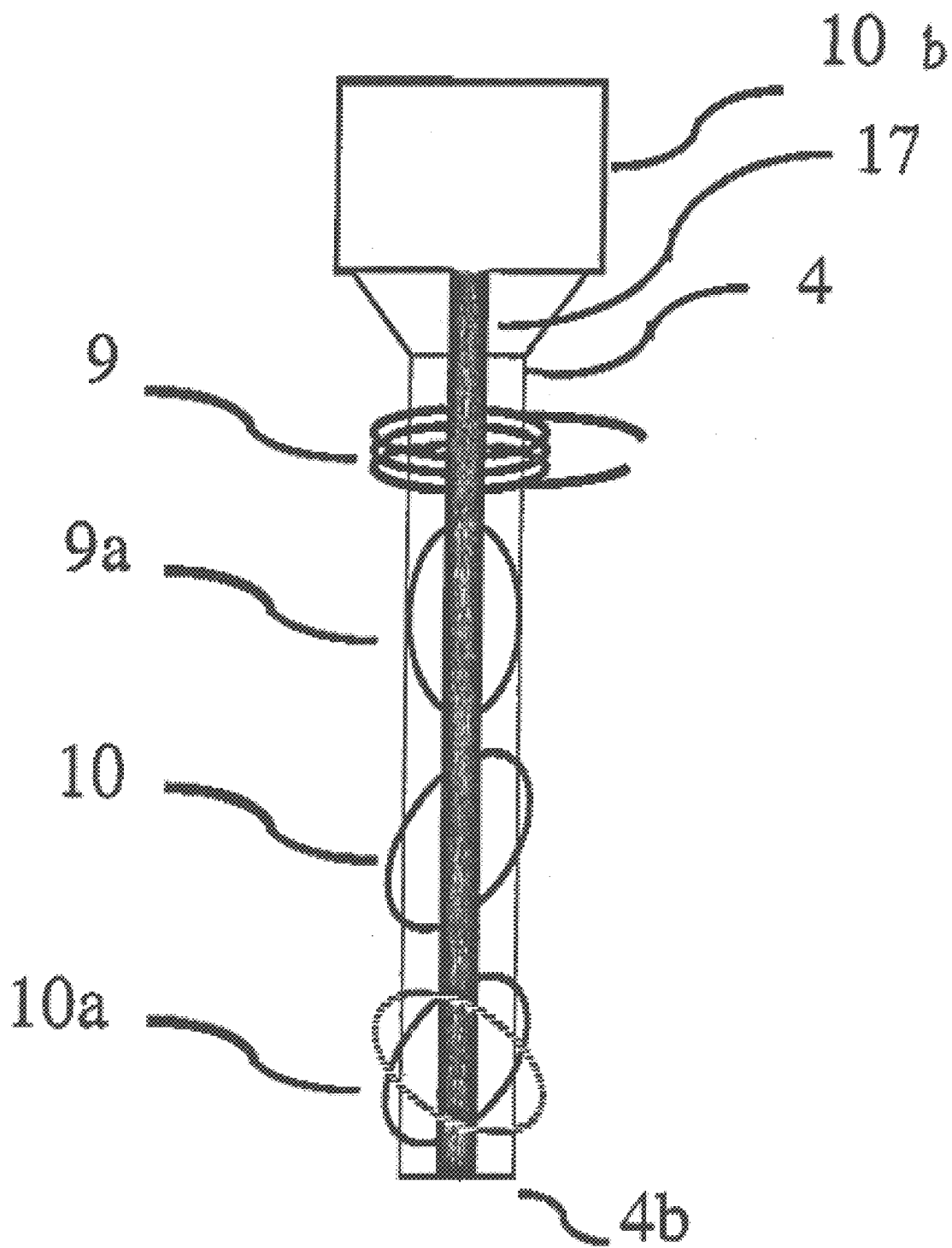
FIG. 4 is a further cross-sectional view of the preferred embodiment of the device which shows the disposition of RF microcoil elements along the distal shaft of the delivery device.

With reference to FIG. 4, active MR visualization of drug delivery is achieved by means of one or more RF microcoils 9, 9a, 10, 10a positioned along the longitudinal axis of the device 4. Particularly preferred is an RF coil consisting of a circular loop of gold or other conductive material 9 positioned around the widest part of the drug delivery device, which would project the field-of vision (FOV) furthermost into the tissue. Depending on orientation of the coil with the magnetic B0, single microcoils may be used separately or may be constructed in an array that may be used together to optimally image the surrounding tissue structure and contrast. In order to reduce the thickness of the RF microcoil, the coil material is sputter-coated onto the surface of the drug delivery device. Preferred also for very small (nanoliter or microliter) injections is a solenoid volume RF microcoil 9a, which by design is sensitive only to the volume inside the coil, said imaging volume being directly related to the diameter of the RF coil. Another preferred MR imaging method which can be used to practice the invention is a combination of RF microcoil and surface coil positioned on the surface of the patient's head. Also preferred is telescoping coil 10 inside of the catheter, expanding it when one wants to image and then withdraw the coil and move on. One may see several cm with this idea. Another preferred method of MR imaging involves the use of an oblong surface loop of wire at the end of a slanted drug delivery device or along the shank of the device, thereby yielding a long FOV. In each of these preferred embodiments of the invention, the transmitting coil would be the head or body volume RF coil inside of the MR imager. The RF surface coil is used only for detection purposes. In another preferred embodiment, a preamplifier 10b positioned near the distal end of the delivery device 4 serves to amplify signals from the RF microcoils 9, 91, 10, 10a.

With further reference to FIGS. 3 and 4, the medical device used in the preferred practice of the present invention for delivery of materials may vary widely with respect to its structure, being highly dependent upon the particular procedural use to which it is being intended. However, there are many features which can be common to all of the devices or which should at least be considered in the various constructions. The simplest device could be a single delivery tube (catheter) which has MR responsive material in or on the composition of the tubing 19, preferably near the distal end or outlet of the delivery tube for assisting in detection by the MR imaging system. The next level of simplified construction would be the presence of MR coils or microcoils 9, 9a, 10, 10a at or near the distal end of the catheter. This again, as elsewhere described, improves the visibility of the viewable signal observable by the MRI system. More than one coil or microcoil may be present, as the distribution of microcoils along a length of the catheter helps define the region within which local signals are detected at efficient intensities. That is, each coil acts as a detector of local MR intensity, and each coil supports a volume around the coil which is observable by MRI systems. The coils may add or integrate their detectable volumes, defining a combined volume which can be efficiently observed by the MR system. As different medical procedures are performed in different environments, with different shapes and different variations in densities, the coils may be located, sized, angled, or otherwise designed to provide specific MR signals and/or responses tailored to the anticipated needs of a particular procedure. In general, the invention is best practiced by employing an array of RF microcoils, such that an image is obtained for any orientation of the drug delivery device.

Figure 3B:
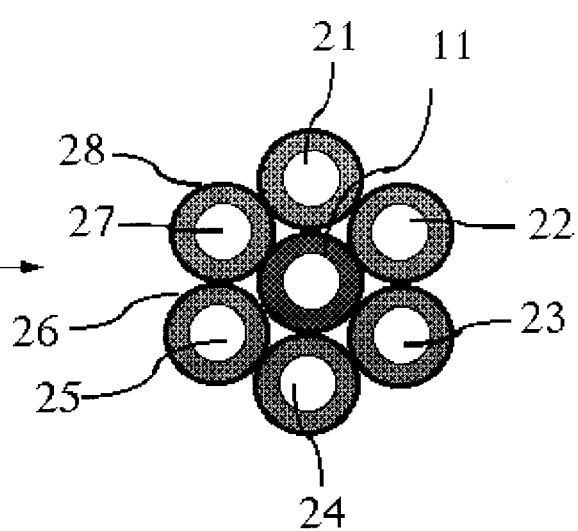
Figure 5:
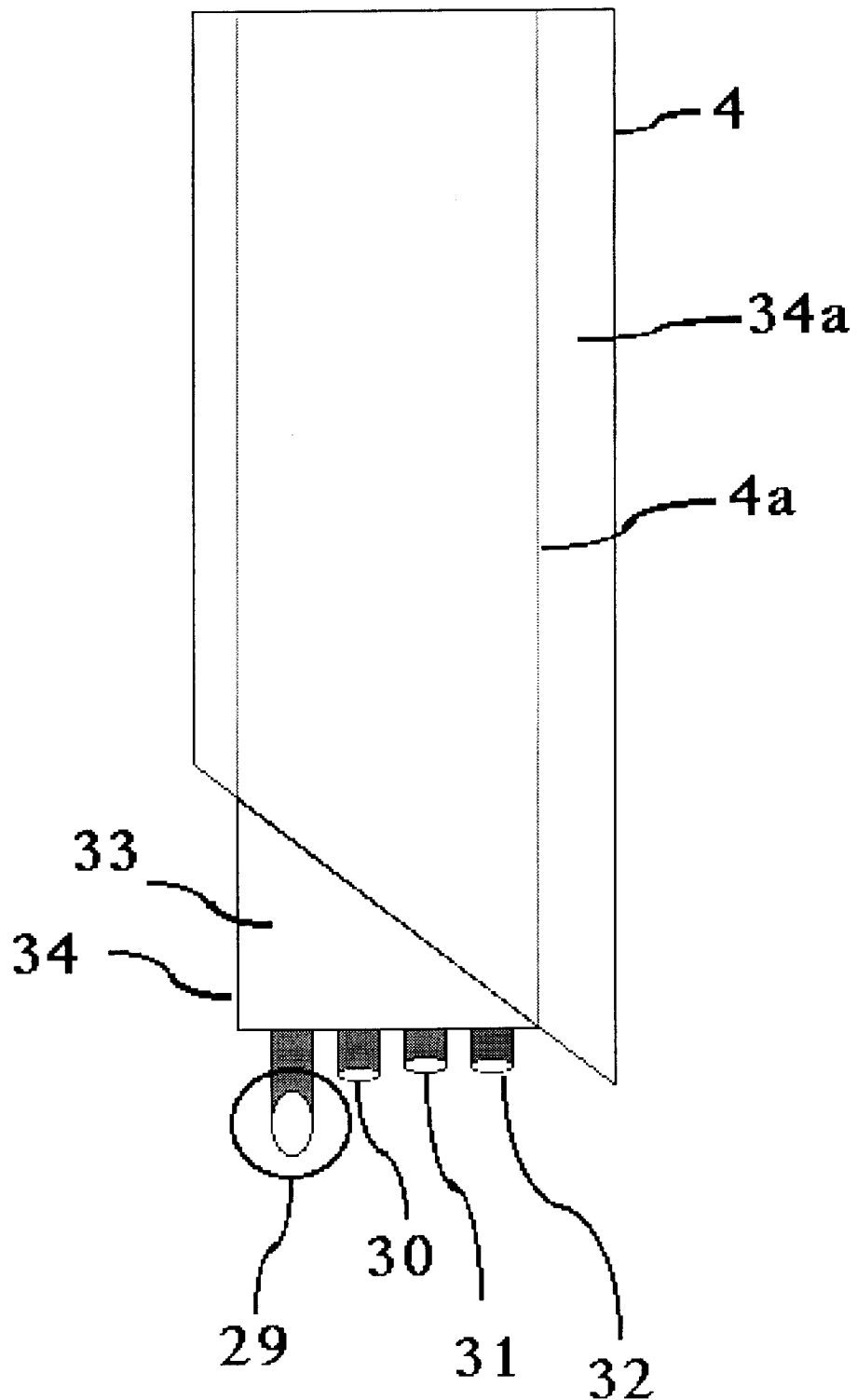
FIG. 5 is an elevated cross-sectional view of the preferred embodiment of the device showing the disposition of the individual tubular probes at the distal tip of the delivery device.

The device may also include numerous catheter elements and/or ports and/or supplemental or independent functional elements. For example, as illustrated in FIG. 3, at least two ports 21, 22 may be needed, one to carry in on chemical material and another to deliver a second distinct chemical material which is or may become desirable during a medical procedure. For example, in addition to a primary treatment chemistry being delivered, saline solutions or specifically tailored solutions to dilute potential oversized deliveries could be desirable. Some treatments may require sequences of drug delivery or delivery of various drugs which may not be storage stable prior to delivery to a patient. Separate ports 23, 24 would be desirable in those events. Additionally, ports may be used to evacuate undesirable materials which are directly or indirectly introduced by the medical procedure. The withdrawal port 25 may comprise a tube with a port which can be attached to negative pressure with respect to the an opening in such a withdrawal port, thus being able to reduce liquid or small particle solids volumes within the area of the procedure. Where the liquid volume or solids are MR viewable, the MR viewable device may be directed towards specific locations or areas and the ports targeted towards those specific areas. In addition, the various ports may be marked or designed to provide distinct signals when viewed by MR systems so that they may be distinguished during performance of the procedures. For example, MR insensitive materials may be used to line a port 26 or materials with different distributions or intensities of MR response may be used in the various ports to differentiate the elements while being observed during performance of procedures. For example, where a withdrawal tube 27 has openings through which materials may be withdrawn, the orientation of that opening within the device becomes important. By lining the edges of the opening with material having unique MR responsiveness within the device 28, the position and orientation of the opening can be readily determined. Particularly preferred is a 2,000–5,000 angstrom thick coating of MR-visible material along the distal shaft of the device.

Where multiple catheters or ports or functional elements are combined into a single device, the configuration of the different components should be tailored for a particular procedure. The different components may be associated by various orientations. As illustrated in FIG. 3B, the most preferred is generally a central tube or tubes with other tubes forming a circular distribution around the central tube or tubes. An MR-visible guidewire may be inserted within the device 4 to assist in positioning the device at a target anatomical location. Particularly preferred is a guidewire or other structural support made of Nitinol™ or other MR-compatible shape memory metal. This is the simplest geometry and provides for smallest diameter sizing of the device. As illustrated in FIG. 5A, other configurations such as parallel alignment of the elements in a strip-like orientation, stacking of elements in rows and columns, or mixtures of these and other configurations may also be useful. Other elements which may be included within the device, in addition to or separate from the use of delivery and/or withdrawal tubes 29, include thermal elements 30 (for providing heat), radiation carrying elements 31 (e.g., ultraviolet radiation, visible radiation, infrared radiation, and even hard radiation carrying elements, such as optical fibers or other internal reflection radiation carrying systems), detection elements 32 (e.g., pH indicators, electronic activity indicators, pressure detectors, ion detectors, thermal detectors, etc.), and any other sensing or detection element which would be useful during medical procedures. These individual elements are each extendable to permit optimal positioning within the tissue would be configured as desired or needed for the particular procedure intended for the device. Procedurally inert elements such as structural supports, reinforcing elements or coatings, back-up elements, and the like, may also be present within the device. Particularly preferred as structural supports or reinforcing elements are circumferential bands of Nitinol or other MR-compatible shape memory metals 35 which, when activated, can facilitate accurate directed placement of the functional tip of the device.

One type of configuration which is presently considered as the preferred embodiment of the invention is the use of a core of element(s) surrounded by a sheath or distribution of additional elements. For example, with further reference to FIGS. 3A and 3B, a central core element my comprise a single tube for delivery of a material, a pair of tubes for delivery of two chemicals, a delivery and withdrawal tube, or a procedurally inert structural support element 11. Around the central core element may be disposed multiple additional elements 21–27, usually seeking as near to a circular distribution about the central core as geometries allow. The attempt at the circular distribution is primarily for purposes of optimizing a small size for the diameter of the article, and is not necessarily a functional aspect to the performance of the device. With respect to FIG. 5, the MR responsive materials, including MR microcoils, may be located within the central core 33, around the central core 34 (beneath any next layering of elements), or over the elements surrounding the central core 34a. Where one or more of the elements receive, transmit or are powered by electrical signals, it is desirable that these elements be electrically separated by either or both of physical separation or additional insulation to prevent mixing or cross-transmission of signals between the distinct elements. Carrying and withdrawing tubes (as well as other elements) may also secondary functions. For example, a carrying tube may be conductive (by being naturally conductive or by having a conductive coating in or outside of the tube) and the electrical connection may be associated with an electronic element or component at the distal end of the device. The tube may thereby act as a carrying tube and electrical connection to the electronic component or element. Structural or adhesive support materials between different elements may also provide such functions. The system may have the material delivery device comprise a catheter assembly of from 2 to 10 independent mass transporting elements.

The various individual elements within the device must be structurally associated, especially away from the distal end, and during insertion, may need structural association at the distal end 11. The structural support or structural integrity may be provided by some physical means of attaching the various elements. This may be done by adhesive materials between the individual elements (which adhesive should be MR compatible), fusion of the various elements, or by coextrusion of the tubes into a single unit (or single component of a multiple element device). The adhesive may be an organic or inorganic adhesive. The distal end of the device may have the ends of the elements temporarily or controllably bonded during insertion. This may be beneficial because it may be desirable to have the individual elements fan out or separate during a medical procedure, for example, as in the case of a target tissue or area of pathology which is anatomically extensive. The adhesive could be water soluble (which would dissolve in a timely manner after insertion), solvent soluble (with solvent delivered into the distal end during a preliminary procedure, or radiation disruptable (e.g., a positive-acting resist adhesive composition which is sensitive to UV, visible or IR radiation which may be delivered through a radiation carrying port). Many other variations and combinations of these considerations and constructions may be used within the practice of the present invention.

Figures 6A, 6B, 6C:
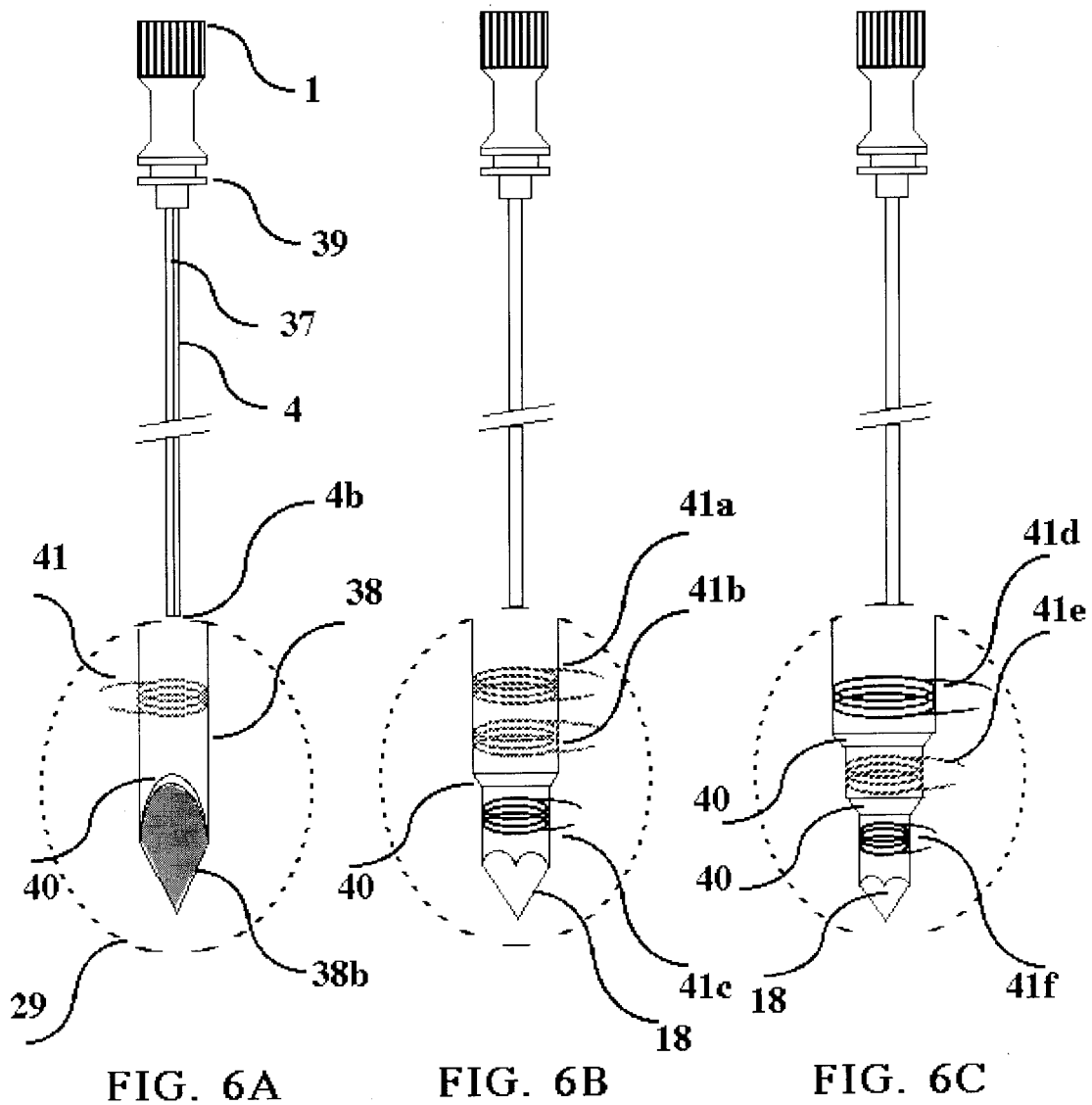
FIGS. 6A, 6B and 6C are side elevational views of the preferred embodiment of the device illustrating the relationship between the RF microcoils and individual tubular components of the distal tip of each drug delivery catheter.
Figure 7:
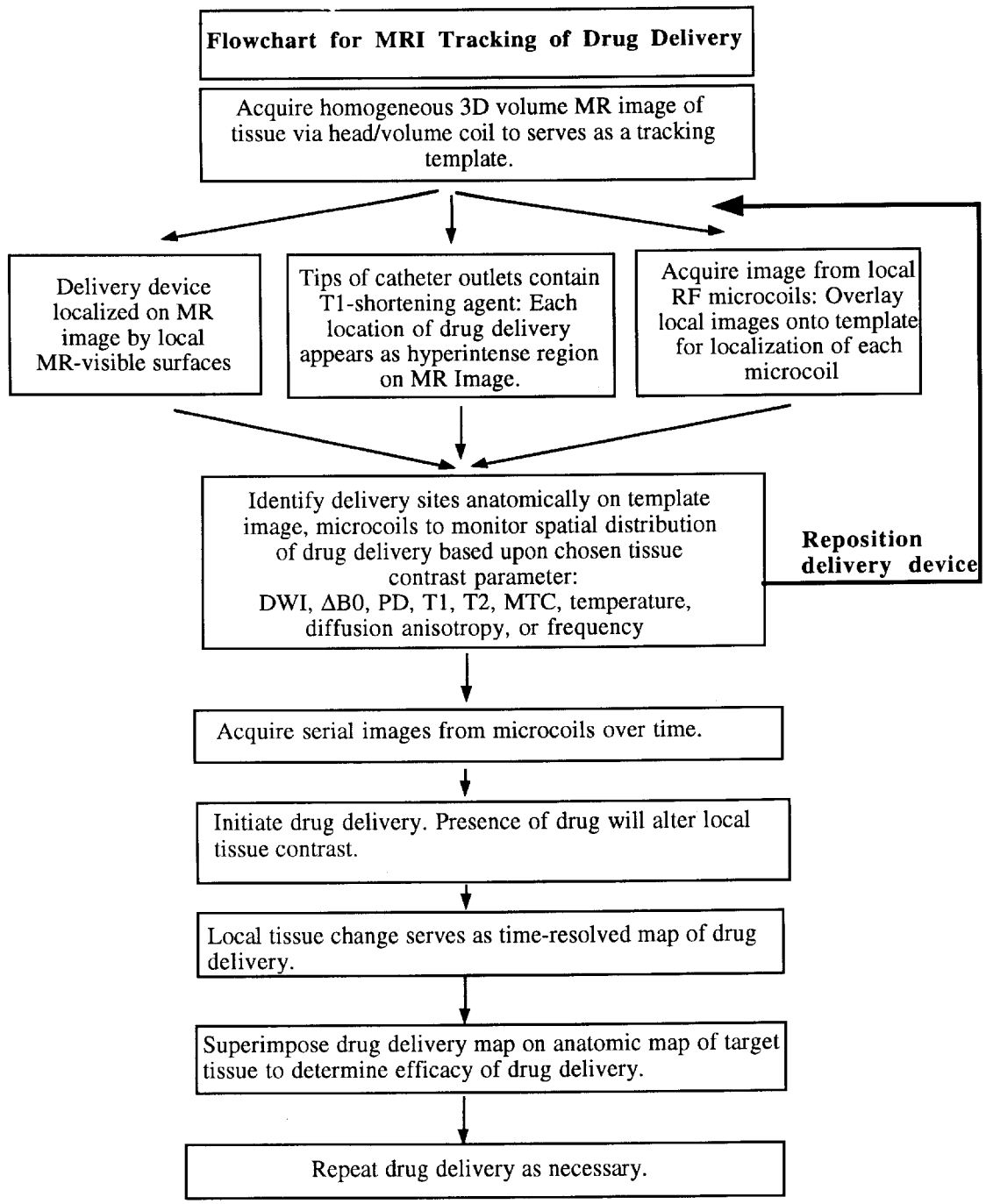
FIG. 7 is a flowchart of the MR imaging methods used to establish the position and orientation of the delivery device, and to track the spatial distribution kinetics of a material injected or infused from the delivery device into tissue.

With reference to FIG. 6a, in another embodiment the dialysis probe is replaced by an MR-visible microcatheter 38, which is a single extrusion catheter made from one of several possible sizes of a polyethylene terephthalate proximal shaft, e.g. 30 ga. The 1–2† mm distal segment of the microcatheter drug delivery device is made of elastomeric hydrogel or similar soft material which minimizes tissue damage during insertion. A plurality of semipermeable membranes 38b are placed circumferentially at regular intervals along the distal segment of the microcatheter, thus enabling wide dispersion of an injected agent, semipermeable membrane consisting of a 0.18–0.22 m$\mu$ millipore filter. The companion microguidewire in this example is made of nitinol or similar memory metal which enables directed placement of the tip of the catheter. The microguidewire 37 is threaded into a clear hub luek-lock cap 39 made of poly-methel-pentene or similar MR-compatible plastic. Both the catheter and guidewire have a linearly arranged array of radiopaque and MR-visible markers 40 disposed at the distal end to provide easily identifiable reference points for trackability and localization under MR imaging and X-ray fluoroscopy guidance. The microcatheter can also be made from any of the well-known soft, biocompatible plastics used in the catheter art such as Percuflex, a trademarked plastic manufactured by Boston Scientific Corporation of Watertown, Mass. With further reference to FIG. 6a of the drawings, when the delivery device is positioned intracranially, the distal markers will be identifiable in an MR image and by X-rays. In another preferred embodiment, two or more RF microcoils are placed along the distal shaft of the microcatheter.

With further reference to FIG. 6 of the drawings, the delivery device can be employed to deliver pharmacologic therapies in order to reduce morbidity and mortality associated with cerebral ischemia, intracranial vasospasm, subarachnoid hemorrhage, and brain tumors. In the method of the invention the distal tip of the multi-lumen catheter assembly is typically positioned a few millimeters above the intracranial target structure using MR imaging. In one preferred embodiment of the invention illustrated in FIGS. 6B and 6C, surface modifications of the material components of the dialysis probe 18 enable timed-release kinetics of MR-visible biologic response modifiers, including peptide macromolecules. In another preferred embodiment of the invention, a pump or other infusion or injection device circulates a solution containing a therapeutic drug or an MR-visible contrast agent through the walls of the dialysis fiber into the brain at rates between 0.01 ul/min to 10 ul/min.

In another preferred embodiment of the invention, pressure ejection techniques well described in the medical literature are used to deliver a predetermined amount of a therapeutic drug agent or MR-visible contrast through one or more of the tubular components of the multi-lumen device. In one specific preferred embodiment of the invention, the catheter is backfilled with the drug or contrast agent, which is functionally connected to a Picospritzer™ (General Valve Corp, Fairfield, N.J.) or a similar instrument that is able to deliver pulses of nitrogen or compressed air with a duration ranging from a few milliseconds to several seconds at a pressure of 10–50 psi. Using such a pressure ejection mode of drug delivery, the concentration of the released substance in the vicinity of the tip is accurately defined by the concentration of the material in the delivery device. A binary solution can also be released, in that two therapeutic or diagnostic compounds can be delivered at the same time by pressure ejection of two materials from two or more separate microcatheters.

In another embodiment of the invention, the MR-visible solution contains sterically stabilized liposomes, with lipophilic or hydrophilic chelators, such as polyaminocarboxylic acids and their salts, such as DTPA on phosphatidyl ethanolamine or steric acid embedded within the external bilayer, or double-label liposomes that chelate a T2-sensitive metal ion within the internal aqueous space and another T1-sensitive metal ion on the outside membrane surface, or liposomes which contain 100–1000 nm air-bubbles, such as argon, carbon dioxide, or air, as a contrast agent. In another preferred embodiment, RF microcoils 41a–f are positioned at the distal ends of individual delivery tubes, said microcoils acting as local MR detectors.

With further reference to FIGS. 1 and 2, in a method of the invention, the implantable MR-visible multilumen catheter includes in another tubing conduit a hydrocephalus pressure valve 1C and self-sealing port 1D preferably made of Nitinol™ or other similar MR-compatible material for regulating the flow of cerebrospinal fluid through the catheter after placement of the catheter tip into cerebral ventricle or other intracranial fluid compartment under MR imaging guidance.

With further reference to FIGS. 1 and 2, in the method of the invention, the implantable MR-visible multilumen catheter also includes in another tubing conduit a metabolic biopsy microcatheter which is used to collect and measure the number of small molecules present in the extracellular fluid, including energy-related metabolites, such as lactate, pyruvate, glucose, adenosine, and inosine, and excitatory amino acids, such as glutamate and aspartate, in a separate reservoir 3b.

With reference to FIG. 7 to FIG. 11 of the drawings, in the method of the invention, MR imaging is used to differentiate normal brain tissues from various pathologic conditions, including solid brain tumor, abscess cavity, edema, necrotic infarcts, reversibly ischemic infarcts, demyelination, and hemorrhage, based on the characteristic ADC of these tissue pathologies already well established in the medical literature. In order to determine the delivery and distribution kinetics of intracerebrovascular, intrathecal, and intraparenchymal injections or infusions of drug or contrast agents within the brain for purposes of creating a means of acquiring a "metabolic" biopsy, a sequence of MR images are collected over a period of time t, which is preferably <100 min and >10 sec. The MR intensity distribution and spatial variation of the calculated ADC of the tissue volume undergoing MR imaging prior to drug delivery is compared with the ADC in the same region following drug delivery in order to determine the efficacy of drug delivery to the targeted intracranial loci.

Methods to obtain absolute measurements of ADC using MR imaging have been described in the medical literature, for example, Moseley et al., Mag. Res. Med., 19, 1991, pp. 321–326, and Moseley et al., Topics Mag. Res. Med., 3, 1991, pp. 50–68). It is well established that if there is restriction to diffusion (e.g. from cell walls), then the measured ADC will decrease with increasing diffusion time. Thus, an express objective of the present invention is to evaluate the efficacy of MR image-guided drug delivery by measuring restricted diffusion with localized MR pulse sequences. In the method of the present invention, modeling of restricted diffusion is used to estimate the size of the diffusion spaces and the permeability of the barriers to drug agents injected into the brain microenvironment. A conventional imaging sequence is repeated with field gradients of increasing strength or duration. The signal decays away exponentially as $e^{-bD}$, where b depends on the strength, duration and timing of the diffusion-sensitizing gradients. However, the diffusion gradients make the sequence extremely sensitive to motion. Thus, in a preferred embodiment of the invention, a navigator echo technique, or its variants, are used to suppress the contaminating effects of patient motion on the ADC measured with MR imaging. In another preferred embodiment, high speed echoplanar imaging is used without movement artifact. In a further preferred embodiment of the present invention, localized measurements of the ADC, $\Delta B0$, T1, T2, MTC, chemical shift frequency, and temperature are acquired from images produced from single-shot or multi-shot stimulated echo (STEAM), gradient echo (GRE or FLASH), or fast spin-echo (FSE) MRI sequences.

In one preferred embodiment of the imaging method of the invention, a 1.5 tesla, 80-cm-bore MR imager with actively shielded gradients of at least 20 mT/m is used to acquire axial diffusion-weighted echoplanar images through a volume of brain tissue one slice at a time, with separate application of diffusion gradients in three orthogonal directions. Trapezoidal diffusion gradients, equal in magnitude and duration, are applied in the vertical (anterior-posterior) direction, and phase-encoding gradients are applied in the horizontal (left-right) direction. A 5-cm field-of-view and 200-kHz continuous readout sampling is preferred, which requires a plateau readout gradient of 12 mT/m. Also preferred are readout gradient trapezoids with 320-microsecond ramps and 640-microsecond plateaus, resulting in 1.28-millisecond readout lobes and 82-millisecond total readout time. The spin echo is placed coincident with the zero-phase-encoded gradient echo. To attain the preferred diffusion gradient of b=600 s/mm2, a spin-echo time of 90 milliseconds was used, and the center of k-space is placed symmetrically. Diffusion-weighted images are preferably acquired as 16 contiguous 1.5 mm slices at 1 slice per second in an interleaved order to minimize magnetization transfer and slice cross-talk effects. At least four diffusion strength, preferably b=10, 207, 414, and 621 s/mm2, should be applied separately in each primary orthogonal direction. Reference scans are acquired without phase-encoding gradients to allow correction of echo position and phase before Fourier transformation reconstruction, to minimize image ghosts. Thus, in the preferred method of the invention, a total of 384 diffusion-weighted echo-planar scans are acquired in approximately 6.4 minutes. The resulting 128×128 images are reconstructed by two-dimensional Fourier transformation. Nominal image resolution is 1.6 mm×2.1 mm×5 mm, giving a 17-uL nominal voxel.

With reference to FIGS. 8–11 of the drawings, in the most preferred embodiment of the MR imaging method of the invention, a therapeutic drug agent is injected from an MR visible drug delivery device into the intraparenchymal extracellular space of the brain. The solution containing the macromolecular drug agent may either form a cavity or infiltrate the extracellular space depending on a number of factors. In either case, subsequent diffusion is governed by the volume fraction (extracellular or pore fraction), the tortuosity of the brain tissue (apparent increase in path length of the diffusing particle), and the diffusion coefficient of the substance itself. A finite and specified concentration of the substance with a finite and specified volume is deposited in the tissue in a period that is effectively instantaneous (i.e. <<time-scale of subsequent diffusion measurements). The injected volume of substance can exhibit at least two distinct behaviors disclosed by MR imaging in the method of the present invention.

Figure 8:
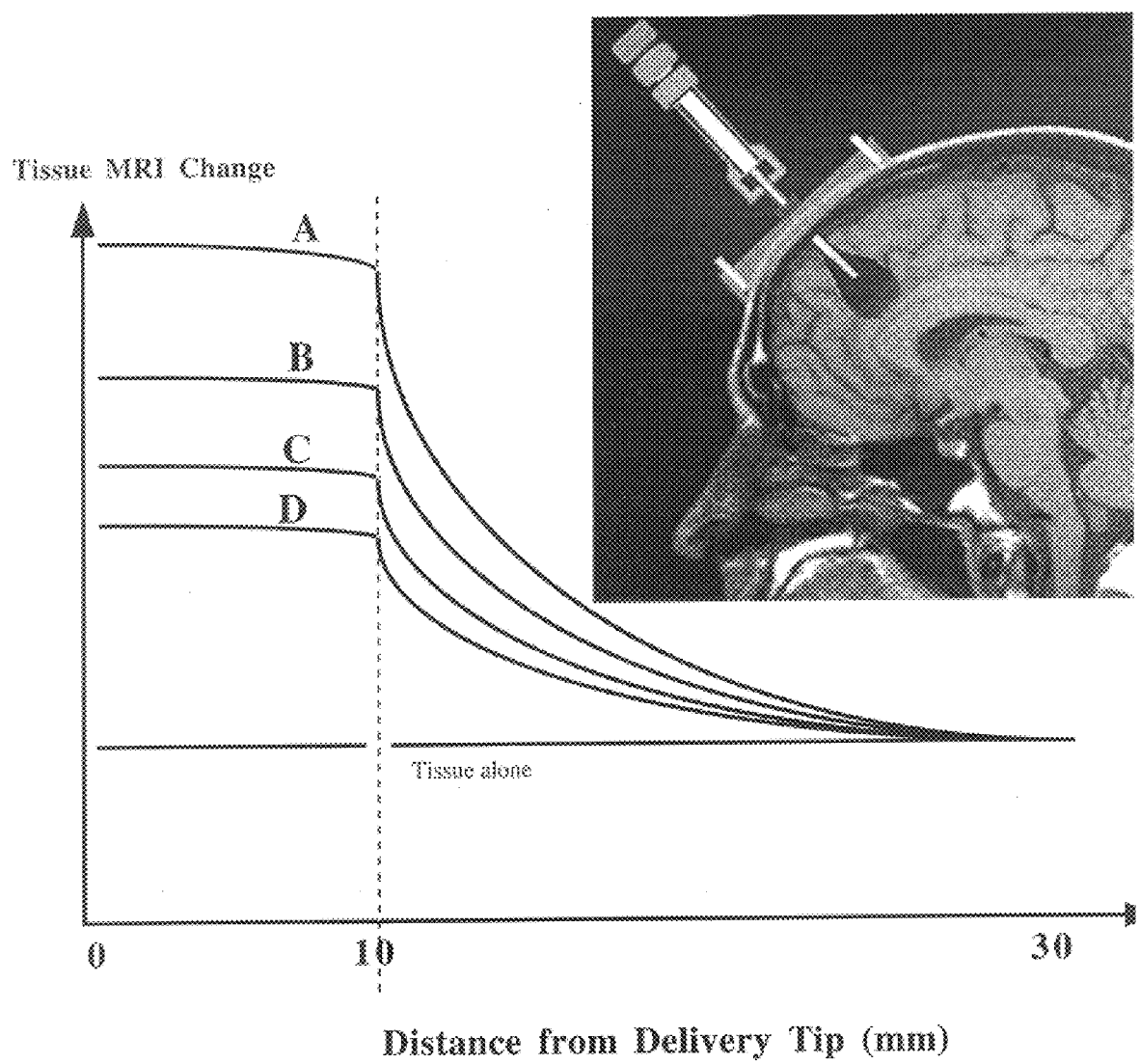
FIG. 8 illustrates how the method of the invention is used to track the spatial distribution kinetics of different drug agents based on their signal intensity decay profiles following injection into a homogeneous cavity in the brain extracellular compartment.

In the first example, summarized in FIG. 8, the injected volume can form a fluid-filled cavity in the tissue, within which the volume fraction and tortuosity take the value of unity which corresponds to a free aqueous solution. Outside this region, the brain tissue has a volume fraction and tortuosity. In this example, diffusion as a function of distance from the injected substance can be represented as a series of curves denoting the concentration as a function of distance from the center of the cavity at successive time intervals. Different drug agents will diffuse at different rates thereby yielding characteristic individual signal intensity delay curves on MR imaging. At the interface between the fluid-filled cavity and surrounding brain tissue two continuity conditions involving flux and concentration apply. Since the amount of material leaving the first region, per unit area of the interface, must be equal to the amount arriving at the second, the phase averages of the fluxes in the two regions must be equal.

Figure 9:
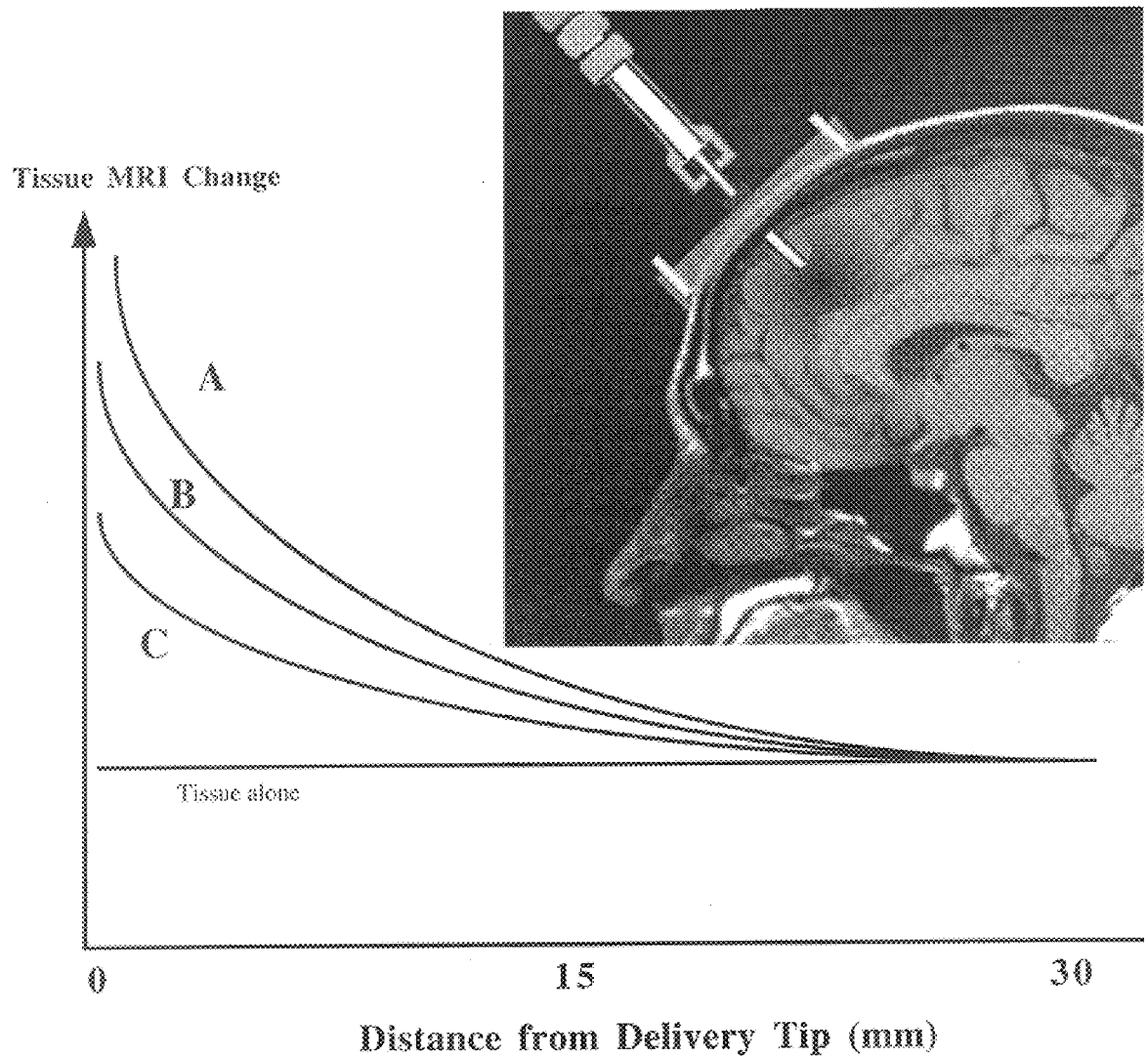
FIG. 9 illustrates how the method of the invention is used to track the spatial distribution kinetics of different drug agents based on their respective signal intensity decay profiles following injection into the heterogeneous extracellular space of the brain.

In the second example, summarized in FIG. 9, the injected material does not form a cavity but instead infiltrates the extracellular space. The diffusion of each agent is related to its molecular weight, molecular radius, and the tissue matrix structure into which the material is injected. Throughout the whole brain tissue, the diffusion behavior is governed by the volume fraction and tortuosity and no discontinuity exists.

Figure 10:
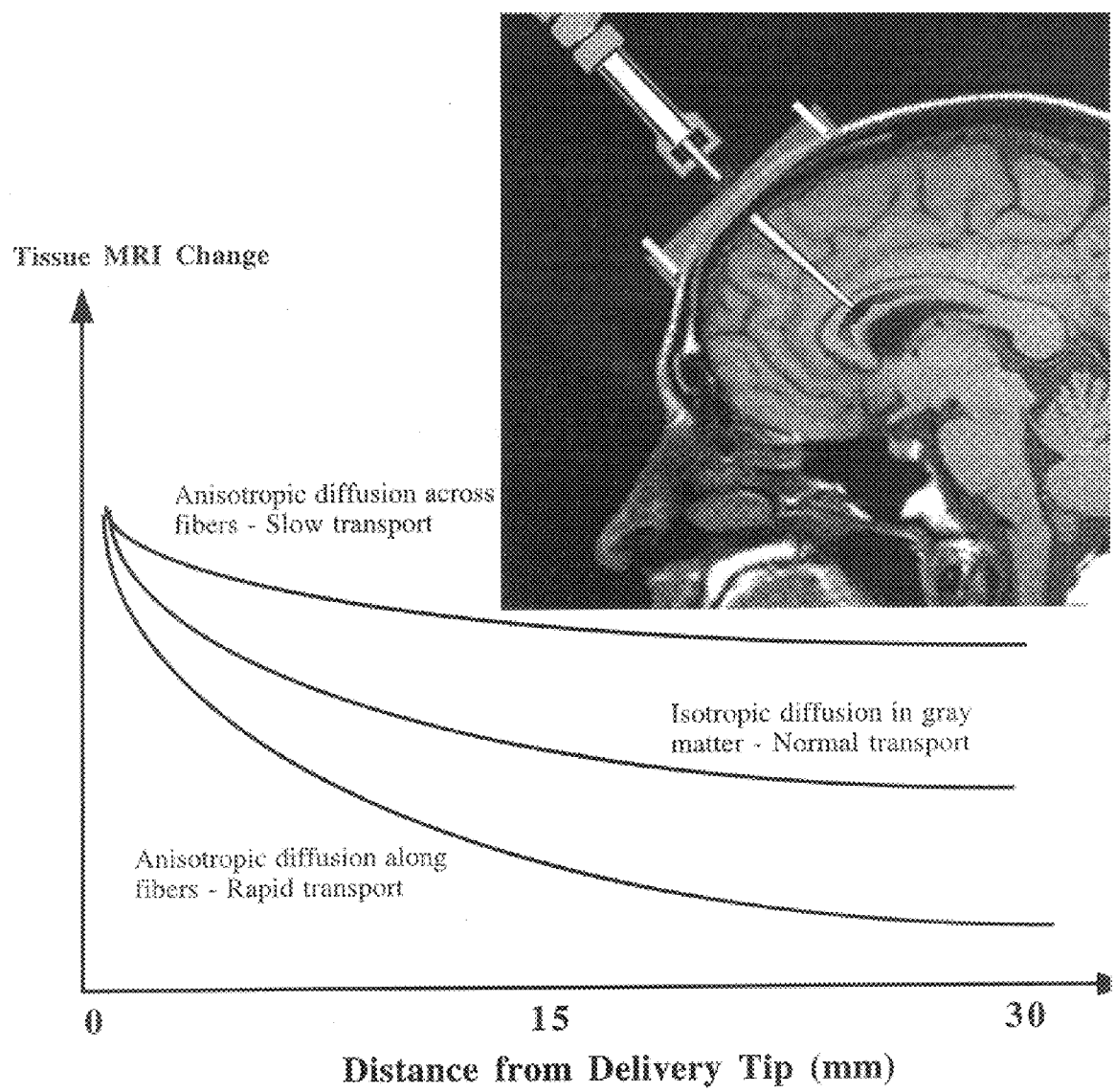
FIG. 10 illustrates how the method of the invention is used to track the spatial distribution of a drug agent that is injected into heterogeneous brain tissue comprised of nerve cells and nerve fibers.
Figure 11:
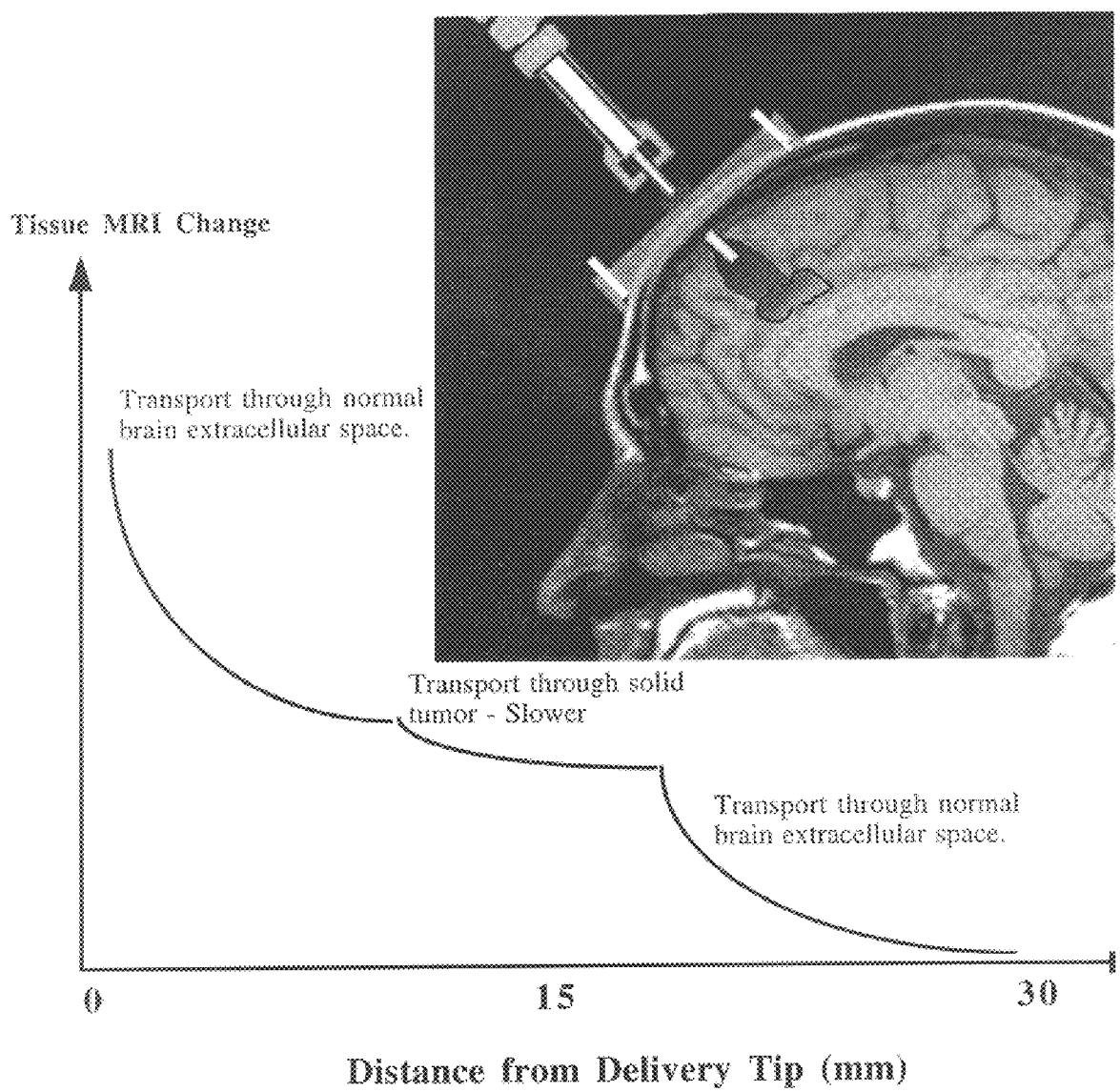
FIG. 11 illustrates how the method of the invention is used to track the spatial distribution of a drug agent injected into the region of a brain tumor.

In the third example of the MR imaging method of the invention summarized in FIG. 10, MR visualization of a drug agent injected into a region of nerve fibers in the brain or spinal cord is performed with diffusion-weighted anisotropic MR imaging. In the preferred method of anisotropic imaging, a 3×3 matrix (tensor) is used, and the signal loss is measured for at least six directions of diffusion gradient. The matrix can be transformed to one that is independent of the directions along which the gradients were applied, and therefore of the orientation of the patient in the magnet. In the preferred method, two measurements are of particular interest. First, the trace of the tensor (i.e. the sum of the diagonal elements) is relatively uniform throughout normal brain, despite its anisotropic structure. It can be thought of as the diffusion coefficient averaged over all directions. Second, an anisotropy index, such as the ratio of the diffusion coefficient in the most freely diffusible direction to that in the least freely diffusible, is highly sensitive to the directionality of the tissue structure. To measure high values in a directional structure the voxel size should be small enough so that there is no averaging of directions within the voxel. Loss of tissue structure is likely to decrease the anisotropy, as the tissue becomes more like a homogenous suspension. Clinical observations of changes in diffusion behavior have been made in multiple sclerosis, in stroke, where the reduction in diffusion precedes the increase in T2, and in experimental epilepsy.

In the fourth example of the MR imaging method of the invention (FIG. 11) macromolecular transport of drugs in tumor tissue is hindered to a lesser extent than in normal tissue, resulting in an altered ADC which enables the visualization of injected drug in neoplastic versus normal tissues.

A catheter system for delivering fluid to a selected site within a tissue comprises a pump for delivering the fluid and a catheter coupled to the pump. The catheter comprises a first tubular portion that has a generally cylindrical lumen of a first internal diameter and is composed of a relatively impermeable material. A second tubular portion that has an open end is disposed within the lumen and a closed distal end is disposed without the lumen. The second tubular portion is composed of a flexible, porous material having a preselected microporosity that is operable to permit fluid to flow from the catheter into the tissue. The second tubular portion is selectively moveable with respect to the first tubular portion. Alternatively, a catheter for delivering fluid to a selected site within a tissue comprises a first tubular portion that has a generally cylindrical lumen of a first internal diameter and is composed of a relatively impermeable material. A second tubular portion that has an open end is disposed within the lumen and a closed distal end is disposed without the lumen. The second tubular portion is composed of a flexible, porous material that has a semi-permeable membrane with pre-selected molecular weight exclusion that is operable to permit fluid to flow from the catheter into the organism. The second tubular portion is selectively moveable with respect to the first tubular portion.

What is claimed is:

1. A system for observing delivery of material into tissue of a living patient comprising:

a) a magnetic resonance imaging system comprising a magnetic resonance source, a magnetic resonance signal reader capable of reading magnetic resonance amplitude, and a device capable of providing a visible image of a magnetic resonance signal from said magnetic resonance signal reader, b) a material delivery device which can be placed within tissue of a living patient and which places magnetic resonance readable material within said tissue of a living patient within an area or volume within of tissue of said living patient and which said magnetic resonance signal reader reads magnetic resonance amplitude within said tissue of a living patient by magnetic resonance imaging, and c) a source of material to be delivered by said material delivery device attached to said material delivery device so that at least some of said material may be delivered by said device into said tissue,, said material comprising material which is capable of affecting the amplitude of an MR signal, said material delivery device comprising a catheter system for delivering fluid to a selected site within a tissue comprising:

1) a pump for delivering the fluid;
   2) a catheter coupled to the pump; and
   3) the catheter having a distal and a proximal end, the catheter comprising a first tubular portion and a second tubular portion, the first tubular portion being made from a relatively impermeable material and having a lumen, the second tubular portion having an open end disposed within the distal end of the lumen and a closed end disposed distally of the distal end of the lumen, the second tubular portion being made of a porous material having a semi-permeable membrane with pre-selected molecular weight exclusion that permits fluid to flow through the lumen and out of the catheter through the second tubular portion into the tissue, said semi-permeable membrane being adapted to provide for complete irrigation of any anatomically extensive tissue region.

2. The system of claim 1 wherein said material delivery device comprises a catheter assembly comprising at least two independent lumens.

3. The system of claim 1 wherein said material delivery device comprises a catheter assembly of from 2 to 10 independent mass transporting elements.

4. The system of claim 3 wherein said material delivery device includes at least one light carrying element connected to a light reading system so that light projected into said area provides a signal through said light carrying device to said light reading system.

5. The system of claim 4 wherein a light transmitting element is associated with said material delivery device.

6. The system of claim 4 wherein said material delivery device includes at least one thermally responsive element connected to a reading system for said thermal response so that temperatures or temperature changes within said area provide a signal to said reading system for said thermal response.

7. The system of claim 4 wherein an element capable of providing a charge is part of said material delivery device, said charge when provided being at a location on said material delivery device which assists in orienting of ionic material being delivered by said material delivery device within an area electrostatically near a point of release of said material from said material delivery device.

8. The system of claim 4 wherein a charge providing element is present to deliver electrical charge onto said material delivery device electrostatically near a point of release of said material from said material delivery device.

9. The system of claim 1 wherein said magnetic resonance source provides actively shielded gradients of at least 12 mTesla/m to provide a visible image within an area or volume comprising tissue of said living patient.

10. The system of claim 1 wherein said magnetic resonance source provides actively shielded gradients of at least 20 mTesla/m.

11. The system of claim 1 wherein said magnetic resonance source provides diffusion gradients of at least 600 s/mm$^2$ to provide a visible image within an area or volume comprising tissue of said living patient.

12. The system of claim 1 wherein said magnetic resonance source provides a magnetic field of at least about 1.5 Tesla.

13. The system of claim 1 wherein said magnetic resonance source provides delivery of said material as brain intraparenchymal delivery of drugs.

14. The process of claim 13 wherein said brain intraparenchymal delivery of drugs is performed without endovascular administration of drugs.

15. A medical device for use with magnetic resonance imaging comprising at least two medical elements which are attached to each other, each of said at least two medical elements providing different medical treatment functions, at least one of said at least two medical elements comprising a hollow tube of a first material, said hollow tube having a proximal end and a distal end, at least one of said at least two medical elements having within its distal end at least one second material having a response to magnetic resonance imaging which is greater than a response provided by said first material wherein said hollow tube comprises a core of said medical device around which at least three other distinct components are physically attached to said core.

16. The medical device of claim 15 wherein at least one of said at least three distinct components of said medical device is selected from the group consisting of radiation transmitting elements and thermal transmission or generating elements.

17. The medical device of claim 16, wherein in addition to said at least one of said at least three components, there is a structural support element which is not capable of providing any function selected from the group consisting of radiation transmitting elements and thermal transmission or generating elements.

18. The medical device of claim 15, wherein at least one of said at least two medical elements comprises a metabolic biopsy catheter and at least another one of said at least two medical elements comprises a drug delivery catheter.

19. The medical device of claim 15 wherein at least one of said at least two medical elements comprises a light carrying element connected to a light reading element and at least another one of said at least two medical elements comprises a drug delivery catheter.

20. The medical device of claim 19 wherein at least one of said at least two medical elements comprises a light carrying element connected to a light reading element and at least another one of said at least two medical elements comprises a drug delivery catheter.

21. A medical device for use with magnetic resonance imaging comprising at least two medical elements which are attached to each other, each of said at least two medical elements providing different medical treatment functions, at least one of said at least two medical elements comprising a hollow tube of a first material, said hollow tube having a proximal end and a distal end, at least one of said at least two medical elements having within its distal end at least one second material having a response to magnetic resonance imaging which is greater than a response provided by said first material wherein said hollow tube comprises a core of said medical device around which at least three other distinct components are physically attached to said core, and a preamplifier is present on said device with said second element being between said preamplifier and said distal end of said device.

22. The medical device of claim 21 wherein said second material comprises a microcoil.

* * * * *